(12) United States Patent
Armato, III et al.

(10) Patent No.: US 6,282,307 B1
(45) Date of Patent: Aug. 28, 2001

(54) METHOD AND SYSTEM FOR THE AUTOMATED DELINEATION OF LUNG REGIONS AND COSTOPHRENIC ANGLES IN CHEST RADIOGRAPHS

(75) Inventors: Samuel G. Armato, III, Chicago; Maryellen L. Giger, Elmhurst; Heber MacMahon, Chicago, all of IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 09/028,518

(22) Filed: Feb. 23, 1998

(51) Int. Cl.$^7$ ........................................... G06K 9/00
(52) U.S. Cl. ............................... 382/132; 382/128
(58) Field of Search ................................. 382/128, 131, 382/132, 199, 172, 266

(56) References Cited

U.S. PATENT DOCUMENTS

| | | | |
|---|---|---|---|
| 4,969,203 | * 11/1990 | Herman | 383/54 |
| 5,068,909 | * 11/1991 | Rutherford et al. | 382/49 |
| 5,638,458 | * 6/1997 | Giger et al. | 382/132 |

OTHER PUBLICATIONS

"Image Feature Analysis for Computer–Aided Diagnosis: Detection of Right and Left Hemidiaphragm Edges and Delineation of Lung Field in Chest Radiographs"; Xin–Wei Xu and Kunio Doi; Medical Physics, vol. 23, No. 9, Sep. 1996; pp. 1613–1624.

\* cited by examiner

Primary Examiner—Matthew C. Bella
(74) Attorney, Agent, or Firm—Oblon, Spivak, McClelland, Maier & Neustadt, P.C.

(57) ABSTRACT

A method, system, and computer product for the automated segmentation of the lung fields and costophrenic angle (CP) regions in posteroanterior (PA) chest radiographs wherein image segmentation based on gray-level threshold analysis is performed by applying an iterative global gray-level thresholding method to a chest image based on the features of a global gray-level histogram. Features of the regions in a binary image constructed at each iteration are identified and analyzed to exclude regions external to the lung fields. The initial lung contours that result from this global process are used to facilitate a local gray-level thresholding method. Individual regions-of-interest (ROIs) are placed along the initial contour. A procedure is implemented to determine the gray-level thresholds to be applied to the pixels within the individual ROIs. The result is a binary image, from which final contours are constructed. Smoothing processes are applied, including a unique adaptation of a rolling ball method. CP angles are identified and delineated by using the lung segmentation contours as a means of placing ROIs that capture the CP angle regions. Contrast-based information is employed on a column-by-column basis to identify initial diaphragm points, and maximum gray-level information is used on a row-by-row basis to identify initial costal points. Analysis of initial diaphragm and costal points allows for appropriate adjustment of CP angle ROI positioning. Polynomial curve-fitting is used to combine the diaphragm and costal points into a continuous, smooth CP angle delineation. This delineation is then spliced into the final lung segmentation contours. In addition, quantitative information derived from the CP angle delineations is used to assess the presence of abnormal CP angles.

27 Claims, 22 Drawing Sheets

METHOD AND SYSTEM FOR THE AUTOMATED DELINEATION OF LUNG REGIONS AND COSTOPHRENIC ANGLES IN CHEST RADIOGRAPHS

The present invention was made in part with U.S. Government support under grant numbers CA48985 and T32 CA09649 from the USPHS. The U.S. Government has certain rights in the invention.

BACKGROUND OF THE INVENTION

1. Field of the Invention

The invention relates generally to a method and system for the computerized, automatic delineation of the lung fields in chest radiographs. Specific application is given for the delineation of the costophrenic angles in digitized chest radiographs. Novel developments and implementations include techniques for delineation and splicing of the costophrenic angles with the segmented lung, and improvements in lung segmentation and the assessment of abnormal asymmetry.

The present invention also relates to CAD techniques for automated detection of abnormalities in digital images, for example as disclosed in one or more of U.S. Pat. Nos. 4,839,807; 4,841,555; 4,851,984; 4,875,165; 4,907,156; 4,918,534; 5,072,384; 5,133,020; 5,150,292; 5,224,177; 5,289,374; 5,319,549; 5,343,390; 5,359,513; 5,452,367; 5,463,548; 5,491,627; 5,537,485; 5,598,481; 5,622,171; 5,638,458; 5,657,362; 5,666,434; 5,673,332; 5,668,888; 6,088,473 as well as U.S. application Ser. Nos. 08/158,388; 08/173,935; 08/220,917; 08/398,307; 08/428,867; 08/523,210; 08/536,149; 08/536,450; 08/515,798; 08/562,188; 08/562,087; 08/757,611; 08/758,438; 08/900,191; 08/900,361; 08/900,362; 08/900,188; 08/900,192; 08/900,189; 08/979,623; 08/979,639; 08/982,282; and 09/027,468, each of which are incorporated herein by reference in their entirety.

The present invention also relates to technologies referenced and described in the references identified in the appended APPENDIX and cross-referenced throughout the specification by reference to the number, in brackets, of the respective reference listed in the APPENDIX, the entire contents of which, including the related patents and applications listed above and references listed in the APPENDIX, are incorporated herein by reference.

2. Discussion of the Background

The utility of image processing techniques in diagnostic radiology of the chest has become more pronounced with the growing acceptance of digital radiography, including both direct-digital acquisition and conventional film acquisition with subsequent digitization [1]. Techniques for image enhancement such as density correction and unsharp masking [2] have, for example, been used to reduce quality variations in portable chest radiographs and to reduce the number of repeat examinations required due to exposure errors [3]. Image compression, image transfer protocols, intelligent long-term storage techniques, and interactive display consoles are currently being developed for use with picture archiving and communication systems (PACS) [4].

Various image processing methods are being assimilated into computer-aided diagnostic (CAD) schemes [5]. Such schemes have been developed for the detection of lung nodules [6–11], interstitial infiltrates [8,12–14,11], pneumothoraces [15], cardiomegaly [16,17], and interval change [18].

Inherent in all these schemes is an underlying knowledge of the lung field location in the digital chest radiograph. This has been achieved through the automated detection of intercostal spaces [19], rib borders [20–22], the ribcage edge [23], and the complete lung boundary [24,25]. To detect intercostal spaces, Powell et al. utilized vertical gray-level profiles, to which shift-variant sinusoidal functions were fit [19]. Sanada et al. employed a similar method to detect posterior rib borders [21]. Statistical analysis of edge gradients and their orientations was then performed within small regions-of-interest (ROIs) to detect subtle continuous rib edges. Wechsler and Sklansky fit linear, parabolic, and elliptical curve segments to the output of gradient and threshold operators to delineate the boundaries of anterior and posterior ribs [20]. Chen et al. used edge gradient analysis to determine whether ROIs used for lung texture analysis overlapped rib edges [22]. Xu and Doi analyzed the first and second derivatives of gray-level profiles to delineate the ribcage edge [23]. Polynomial functions were then fit to initially detected edges. Cheng and Goldberg applied a clustering algorithm to the gray-level histogram computed from a selected region of an image to identify a single gray-level threshold for lung segmentation. The resulting borders were then refined using linear and parabolic curve-fitting techniques. Pietka delineated lung borders using a single threshold determined from the gray-level histogram of a selected region [25]. Gradient analysis was then employed to extend the edges.

Others have directly addressed the segmentation of lung fields for the detection of abnormal asymmetry [26], for the development of radiographic equalization techniques [27], or for use with region-specific display enhancement techniques [28–30]. Duryea and Boone devised a lung segmentation method based on gray-level profiles and contrast information [27]. To selectively enhance the mediastinum and subdiaphragm, Sherrier and Johnson applied histogram equalization techniques to areas determined through local gray-level histogram analysis to be within these regions [28]. Sezan et al. identified a lung/mediastinum threshold in the gray-level histogram to perform adaptive unsharp masking in these different anatomic regions [29]. McNitt-Gray et al. developed a pattern classification scheme implementing stepwise discriminant analysis as a basis for feature selection, which was then used to train classifiers [30]. Clearly, automated segmentation of the lung fields in chest images has many practical applications in addition to its role as a foundation for various CAD schemes.

With the exception of interval change detection, most CAD schemes currently being developed for digital chest radiography are specific to one particular pathology. These schemes often utilize a priori information regarding the "normal" appearance of the ribcage, diaphragm, and mediastinum in a chest image. A potential problem arises when the nature of the thoracic abnormality is such that it substantially affects the volume of the lungs. A large-scale abnormality of this type will usually cause abnormal asymmetry on the radiograph due to a substantial decrease in the area of the aerated lung field (i.e., the high optical density region associated with the normally low attenuation of the lungs) in one hemithorax as projected onto the radiograph. This can substantially alter the overall morphology of the thorax, which, while apparent to a radiologist, could result in the failure of computerized schemes. Such abnormalities would include dense infiltrates, substantial pleural effusions, large neoplasms, extensive atelectasis, pneumonectomy, elevated hemidiaphragm, or cardiomegaly.

A normal PA chest radiograph acquired with the patient properly positioned demonstrates two well-defined CP angles, which represent radiographic projections of the costodiaphragmatic recesses. The costal and diaphragmatic aspects of the normal CP angle converge to form a typically sharp, acute angle. Any observed deviations from this configuration may provide the radiologist with important diagnostic information.

A variety of physical and pathologic conditions may be manifested in the CP angle. In the upright chest examination, for example, non-loculated fluid in the pleural space will collect under the influence of gravity in the costodiaphragmatic recess. Such a pleural effusion will radiographically alter the appearance of the CP angle by blunting the normally sharp appearance of the anatomic recess [31,32]. In another example, the characteristic flattening of the diaphragm present in patients with emphysema will typically extend into the CP angle region, causing the costal and diaphragmatic aspects of the CP angle to converge at a less acute angle [31,34]. In addition, fibrotic or infiltrative processes in the lung bases may simply obscure the CP angle [35].

SUMMARY OF THE INVENTION

Accordingly, an object of this invention is to provide an improved method and system for segmenting lung fields in chest images.

It is another object of the present invention to provide an automated method and system for the delineation and/or quantitative analysis of the costophrenic angles in chest images.

It is yet another object of the present invention to provide a method and system for integrating delineated costophrenic angles with lung fields in order to better define the lung field and/or asymmetries.

These and other objects are achieved according to the present invention by providing a new and improved method, system, and computer product wherein a global threshold analysis of a PA chest image is performed to create a binary image of the chest region. The lung fields are identified in the chest region, and lung segmentation contours corresponding to the identified lung fields are constructed for the PA chest image.

Delineation and quantitative analysis of the lung fields is performed by generating a digital PA chest image which includes both CP angles. The left and right CP angles are delineated on the PA chest image so that the angle formed by the left and right CP angle margins can be determined.

The delineated CP angles are integrated with the lung fields in order to better define the lung fields and/or asymmetries. Once an initial set of lung segmentation contours is determined, the CP angle margins are separately delineated. The CP angle margins are then spliced to the initial set of lung segmentation contours to produce a final set of lung segmentation contours.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

A method for accurately segmenting the aerated lung fields in posteroanterior (PA) chest images can be used to detect the presence of abnormal asymmetry. Detection of these abnormalities are useful in CAD schemes for digital chest radiography and in prioritizing abnormal cases in a PACS environment.

In conjunction with our lung segmentation method, we have developed a technique for delineating the CP angle margin in PA chest images [36]. The contour segments so delineated are automatically spliced into the final contours encompassing the aerated lung fields. Not only does the CP angle delineation technique result in contours that more accurately capture a clinically important anatomic region, but it is capable of rectifying lung contours that might otherwise fail to provide an acceptable segmentation. Consequently, the CP angle delineation technique is an integral part of the overall lung segmentation scheme.

We have explored the potential benefit of the CP angle delineation technique as an independent CAD tool. Quantitative measurements of the angle formed by the delineated costal and diaphragmatic margins provide a measure of CP angle blunting or obscuration. We have employed these computer-determined measurements to identify abnormal CP angles. While the task of identifying a CP angle is straightforward for a human observer, blunting of the CP angle may be overlooked by a radiologist during clinical interpretation, especially when the lung fields are being scrutinized for other pathology. Moreover, quantification of this anatomic region will provide radiologists with additional diagnostic information. As primary interpretation from display monitors gains acceptance, a variety of automated analyses will routinely be performed prior to the radiologist viewing the images; assessment of the CP angles represents another such computational tool.

Therefore, we have developed a fully automated technique for segmenting the aerated lung fields in PA chest images. An independent technique is applied to more accurately include the CP angles in the segmentation. This segmentation method is robust with regard to the overall morphology of the chest and, in addition, is well-suited for detecting abnormal asymmetry in PA chest images.

Figure 1:
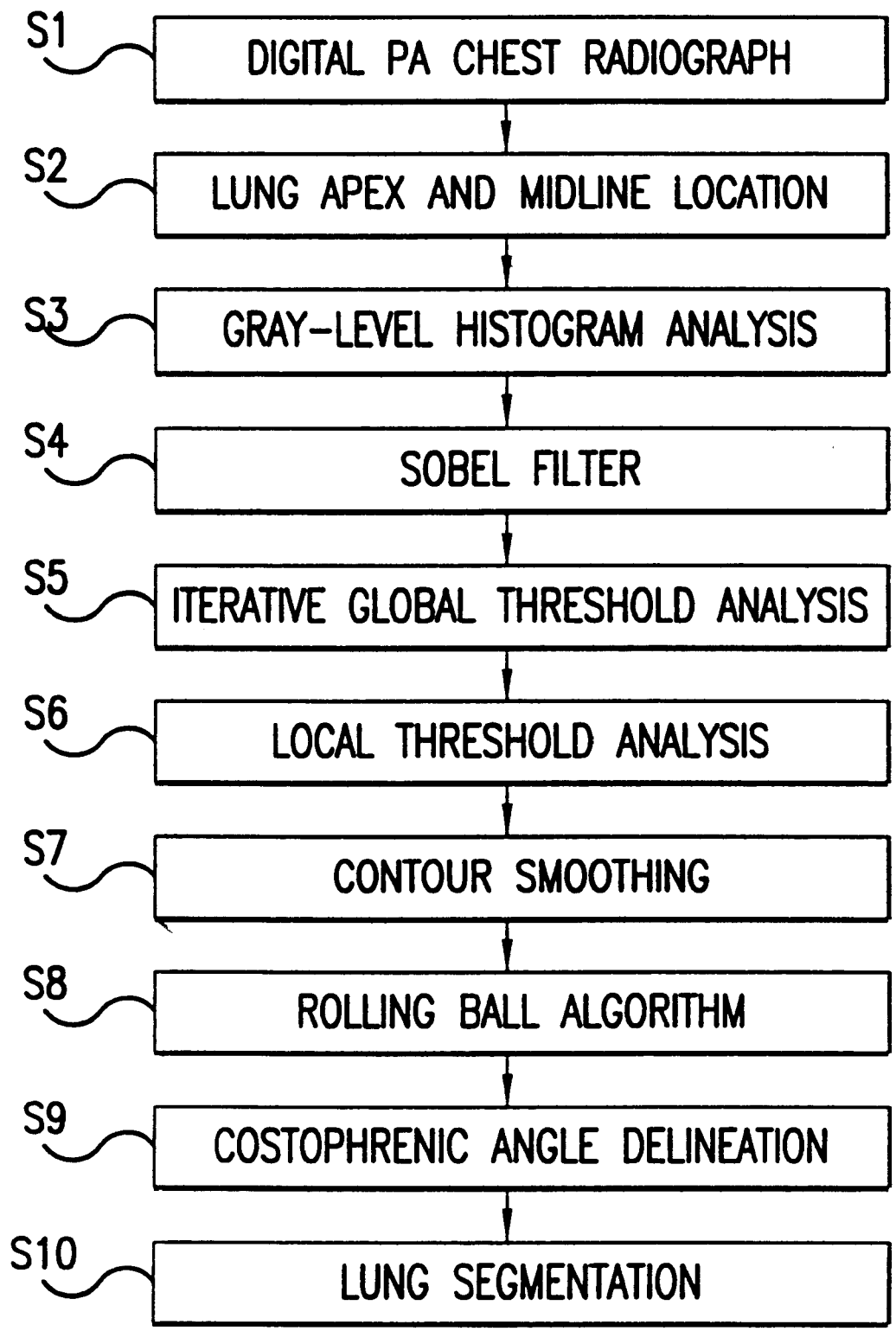
FIG. 1 is a flowchart illustrating the automated method for the segmentation of the aerated lung fields in digital chest radiographs.

Referring now to the drawings, and more particularly to FIG. 1 thereof, a flowchart provides an overview of the automated method for the delineation of the lung fields and the assessment of the costophrenic angle in chest images. The overall scheme includes an initial acquisition of a radiographic image and digitization in step S1. Then, in step S2, horizontal gray-level profile analysis is used to determine the location of the lung apices and the midline in the image. Next, in step S3 a gray-level histogram is constructed from a large rectangular ROI located near the central portion of the image. The maxima and minima of this histogram are analyzed to identify a range of gray-levels that will be used during the iterative global gray-level thresholding process. In step S4 Sobel filtering is applied to the image. Then, in step S5 iterative global gray-level threshold analysis is performed. Seven iterations are performed using progressively larger gray-level thresholds from the identified gray-level range [26]. At each iteration, a binary image is constructed in which only pixels having a corresponding image pixel gray-level less than the threshold are turned "on". An eight-point connectivity scheme is employed to construct contours around each group of contiguous "on" pixels. Gray-level profiles constructed through the center-of-mass (centroid) of each such contour are analyzed to determine whether the contour encompasses pixels belonging to the lung fields. Pixels in contours determined to be outside the lung fields are prevented from contributing to binary images created at later iterations. A set of initial contours results after the seventh iteration. To capture the aerated lung field more completely, in step S6 a local gray-level thresholding technique is implemented along the initial contours. A final contour set is constructed based on a composite binary image created by thresholding pixels within the individual local ROIs. Next, in step S7 the contours are smoothed, and then, in step S8 a rolling ball algorithm is employed to eliminate large-scale irregularities in the contours. Lung segmentation is completed in step S10 after a procedure for delineating the costophrenic (CP) angles is applied in step S9.

Horizontal gray-level profiles are analyzed to determine the location of the patient midline and the lung apices in each image. The midline position is used throughout the scheme to distinguish between right and left hemithoraces. The apex location effectively identifies an upper bound in the image above which no lung pixels are expected to exist.

A series of row-averaged horizontal gray-level profiles is constructed for the upper one-third of the image by considering groups of rows five at a time. The profiles are then analyzed for gray-level maxima and minima. Centrally located maxima are identified in each profile, which will contain two such maxima if the trachea is prominent or a single maximum otherwise. The midline position is defined as the average x-position of all such maxima in all profiles.

Figure 2:
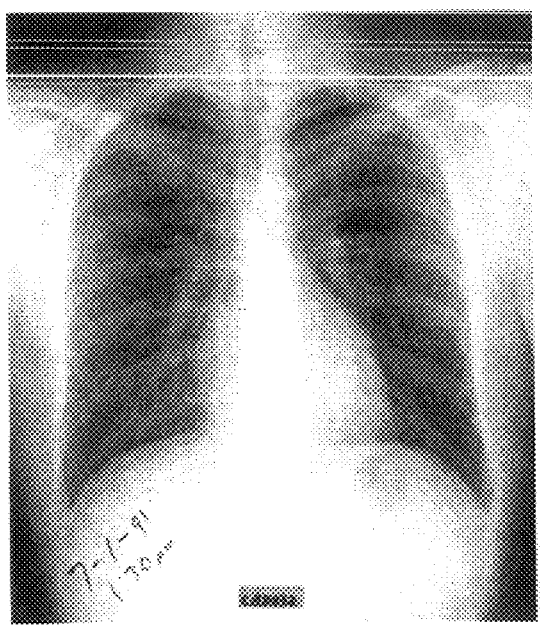
FIG. 2 is a photograph/illustration which demonstrates the lung apex and midline determination, with row-averaged horizontal gray-level profiles shown for two sets of five consecutive rows.

FIG. 2 shows an image produced as a result of lung apex and midline determination. Row-averaged horizontal gray-level profiles from two sets of five consecutive rows are shown for a normal PA image. The computer-determined lung apex and midline positions are indicated by the bright horizontal line and the vertical line segment, respectively.

The lung apex is located based on the profile minima. Although right and left lung apices may occur at different rows due to patient rotation in the image plane, a single row representing the more superior of the apices is identified to serve as an upper bound on the lung fields in the image. Consequently, both hemithoraces (now distinguished by the midline) are considered separately. The lowest minimum on each side of the midline is identified in all profiles, provided that the gray-level of this minimum is between 15% and 85% of the central maximum gray-level. This range was established by observing that a minimum below 15% is probably within the direct-exposure region, while a minimum above 85% represents a profile deviation that is too minor to consider. The lung apex is then identified as the row corresponding to the first profile such that the lowest minima of the succeeding (i.e., inferior) two profiles have lower gray-levels.

Figure 3:
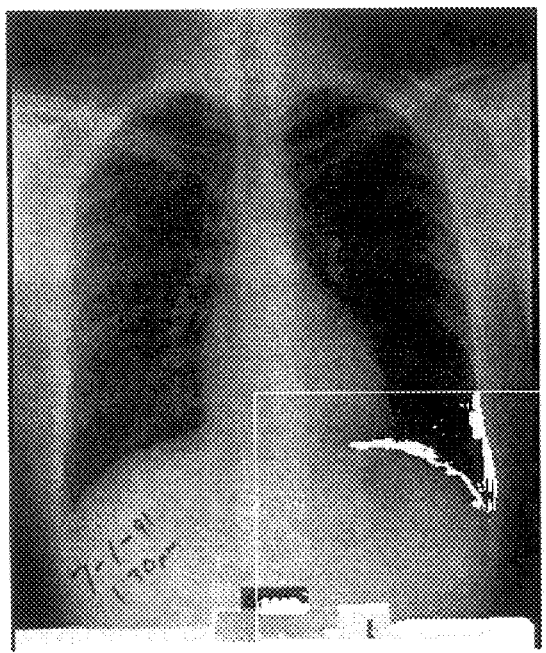
FIG. 3 is a photograph/illustration which demonstrates the result of Sobel filter application to the lower right quadrant of the image shown in FIG. 2.
Figure 2B:
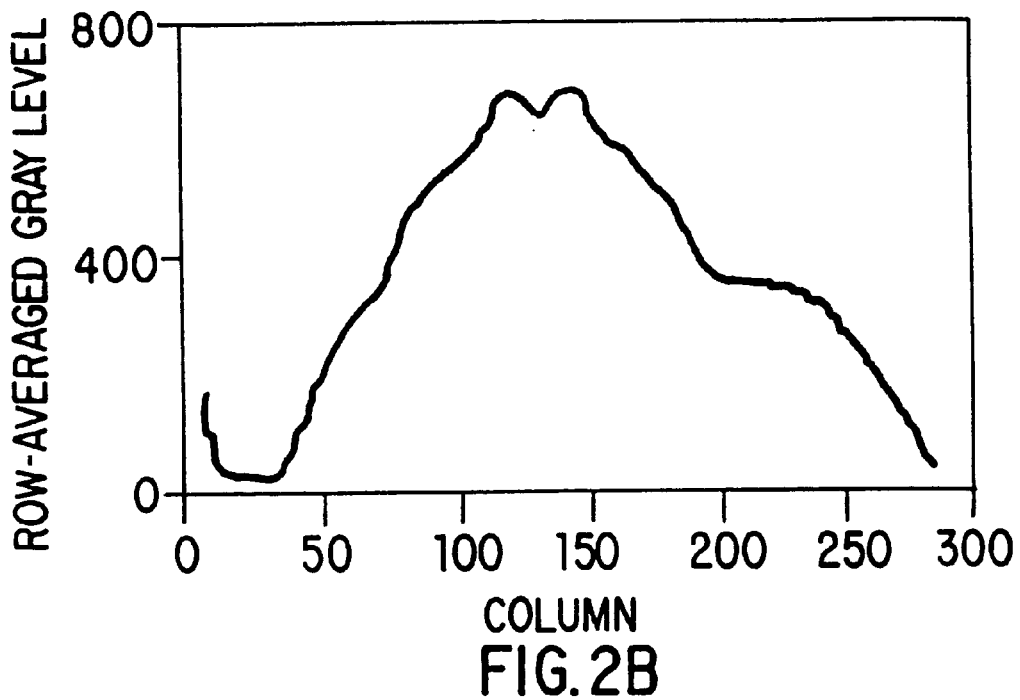
Figure 2C:
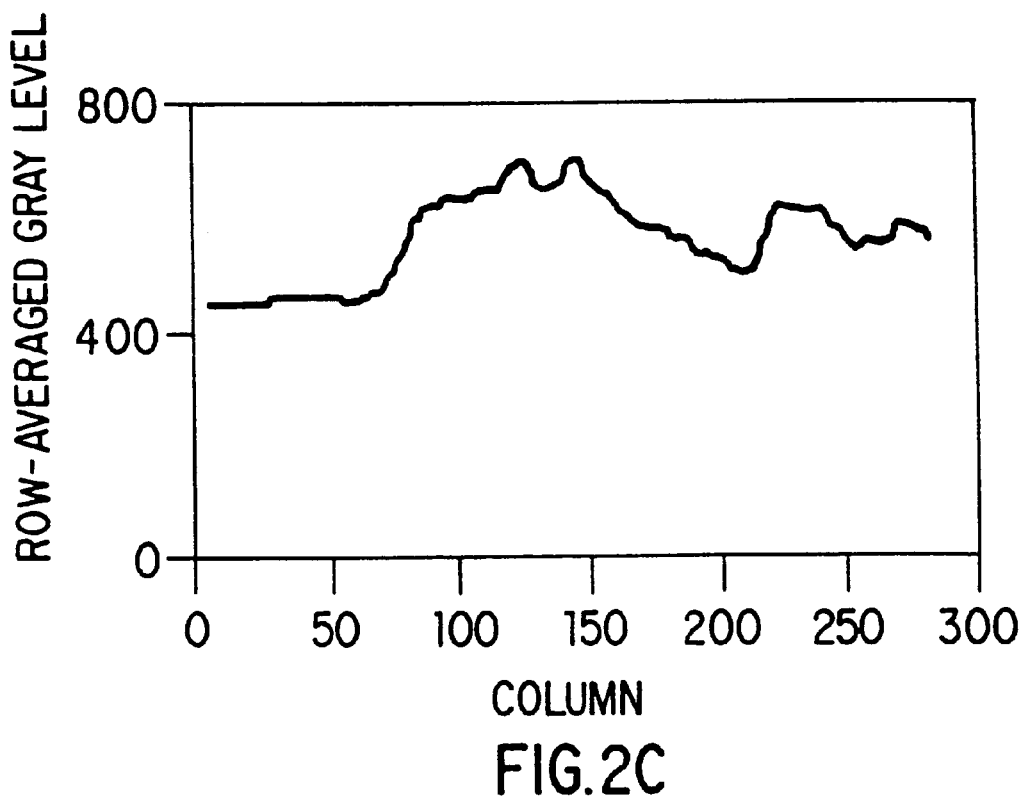

In step S4 a Sobel filter is convolved with the lower right quadrant of the image (i.e., the patient's left side) to accentuate the diaphragm border and the lower ribcage edge, thereby preventing lucencies caused by bowel gas from merging with lung contours at higher gray-level thresholds. Pixels in the image quadrant representing strong, appropriately directed gradients as determined by the filtered images are set to an arbitrary gray-level value of 999 which is high enough to exceed any realistic threshold range identified through global gray-level histogram analysis. This enhancement acts as an artificial boundary that will not allow penetration of the left lung contour. FIG. 3 shows the result of Sobel filter application to the lower right quadrant of the image of FIG. 2. Filtered pixels with values that exceed a threshold are assigned a gray-level of 999 in the image.

Figure 4:
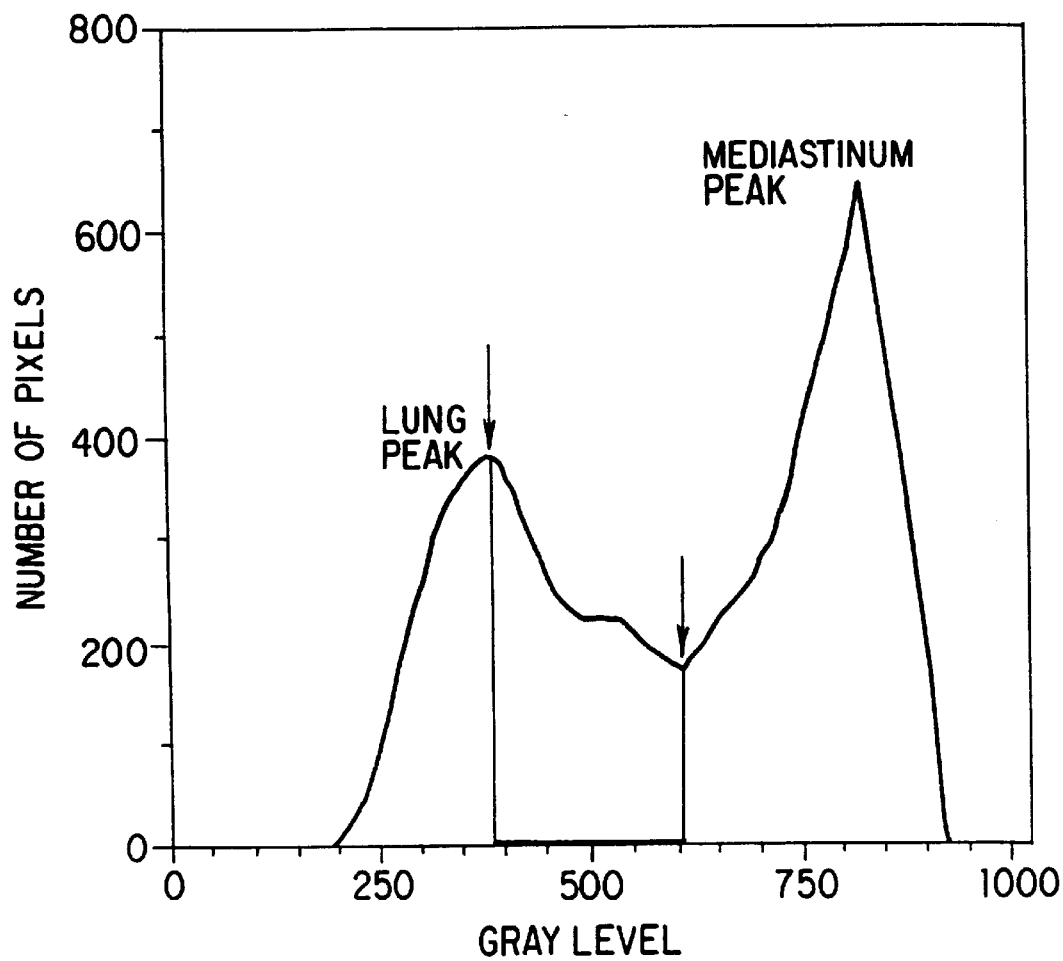
FIG. 4 is a graph illustrating a typical global gray-level histogram for PA chest images, identifying the range of gray-levels used during iterative global gray-level thresholding.

A global gray-level histogram is used to initiate the segmentation scheme. In an effort to obtain more uniform histograms, the calculation of the histogram is limited to a 181×141-pixel region centered 140 pixels from the top of the image, i.e., a region effectively centered over the thorax. A typical region will contain high-density (low gray-level) pixels belonging to lung as well as low-density (high gray-level) pixels belonging to more radio-opaque structures such as the mediastinum, ribcage edge, and diaphragm. Consequently, the histogram resulting from such a region tends to be bimodal, with one peak centered over lower gray-levels (the "lung peak") and another centered over higher gray-levels (the "mediastinum peak"). FIG. 4 is a typical global gray-level histogram demonstrating characteristic bimodal distribution. The arrows indicate the peak containing pixels belonging predominantly to lung and the minimum between the lung and the mediastinum peaks, respectively, as determined by the computer. The arrows mark the range of gray-levels used in the iterative thresholding technique.

Figure 24:
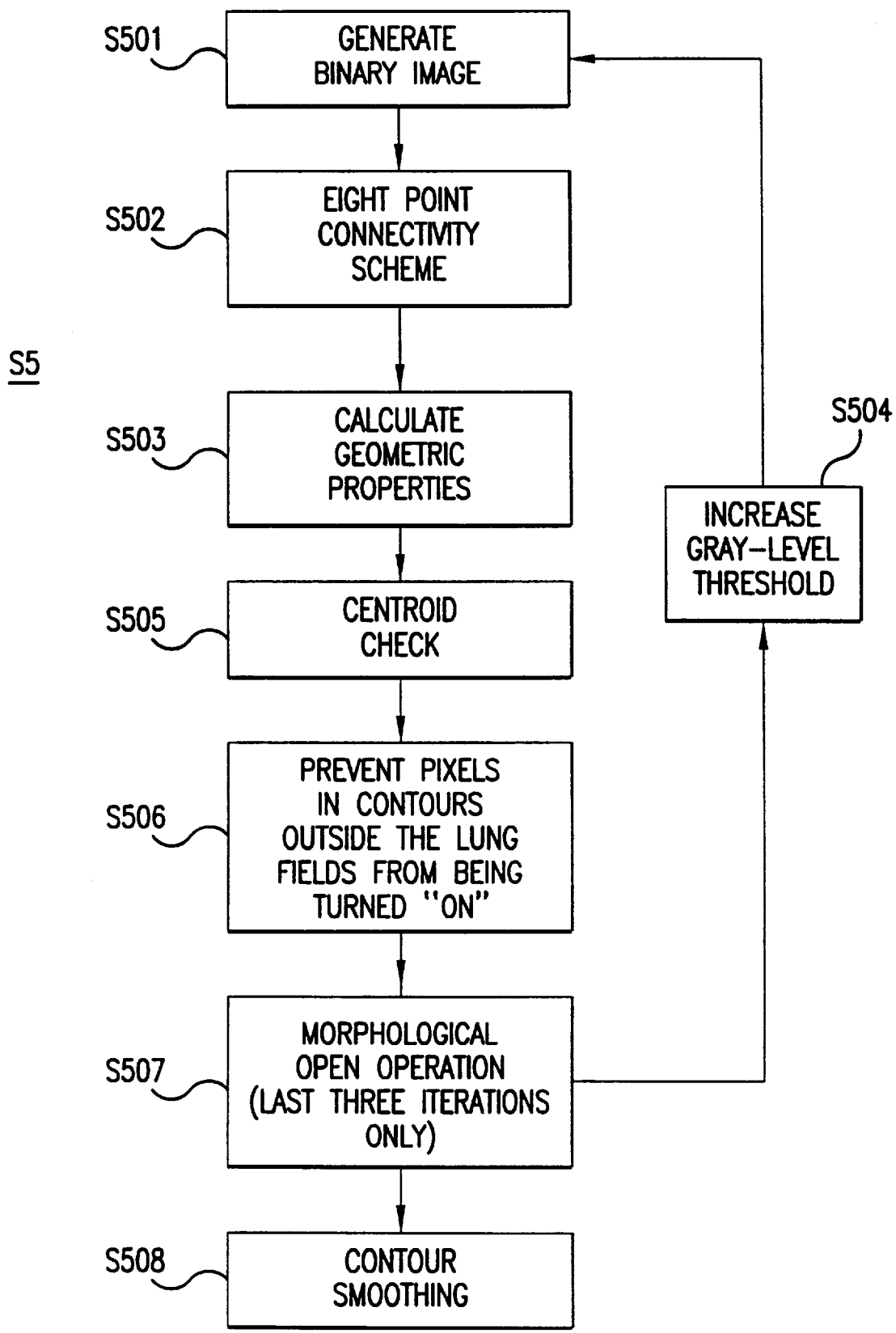
FIG. 24 is a flowchart showing the substeps performed during iterative global gray-level thresholding analysis.

The slope of the global gray-level histogram is used to identify the gray-level at which the lung peak occurs and the gray-level at which the minimum between the lung and mediastinum peaks occurs. These points are used in step S5 to bound a range of gray-levels during iterative global gray-level thresholding. The iterative process is defined by successive thresholding at seven equally spaced gray-levels within the range. Step S5 includes substeps S501 through S508 as shown in FIG. 24.

In substep S501 a binary image is created during the first iteration using the lowest of the seven gray-levels (i.e., the highest optical density of the range) as the threshold value. Pixels are turned "on" in the binary image if the corresponding pixel in the radiographic image has a gray-level less than the threshold. This first threshold will obviously produce a binary image with fewer "on" pixels than any subsequent binary image. The resulting binary image is sent through a contour detection routine, which in substep S502 utilizes an eight-point connectivity scheme to construct contours representing the boundaries of groups of contiguous "on" pixels [38]. Then, in substep S503 the contour detection routine calculates important geometric properties of these contours, such as the center-of-mass (centroid) of the contour, contour compactness, contour length (in terms of pixels), and the area enclosed within the contour (in terms of pixels) [39].

Figure 5A:
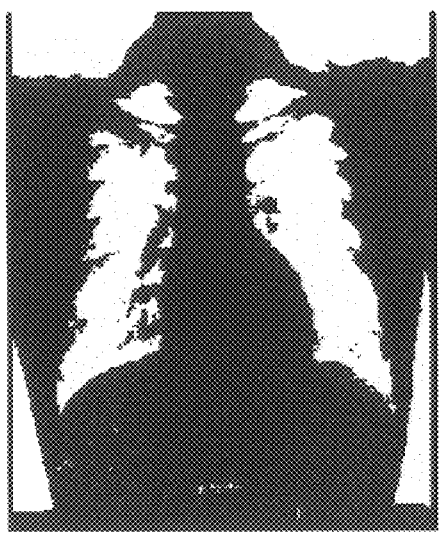
FIGS. 5(a) and 5(b) are photographs/illustrations of two binary images created by thresholding the image shown in FIG. 2 at two different gray-levels.
Figure 5B:
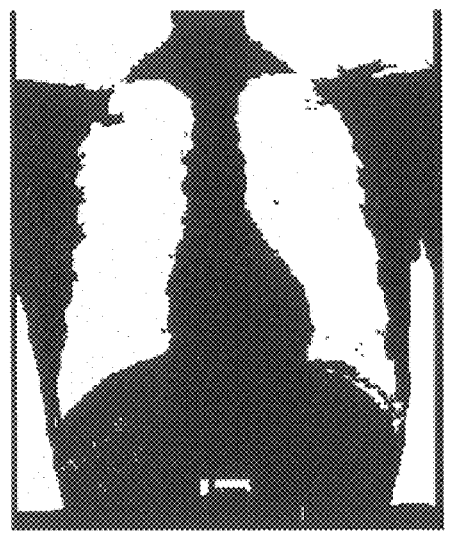

In substep S504 the gray-level threshold is increased for each subsequent iteration. Thus, subsequent iterations create additional binary images based on successively larger gray-level thresholds. FIGS. 5(a) and 5(b) show two binary images created by thresholding the image shown in FIG. 2 at two different gray-levels. A lower gray-level threshold was used to construct FIG. 5(a) than was used to construct FIG. 5(b). Contours are again constructed around regions of contiguous "on" pixels in substep S502, and geometric parameters of each contour are calculated in substep S503.

The iterative aspect of this process encourages proper lung segmentation. For any given threshold value, pixels belonging to the direct exposure region outside the patient will be turned "on" in the binary image (since these pixels will have gray-levels below the lowest gray-level threshold) along with pixels belonging to lung (the pixels of interest, which typically possess relatively low gray-levels). Moreover, at intermediate threshold values, regions such as bowel gas, the trachea, portions of the shoulder, and subcutaneous tissue will also be turned "on". Consequently, unless pixels from these non-lung fields are suppressed, the contours around these regions will merge with the contours encompassing actual lung at the higher threshold values.

Figure 6:
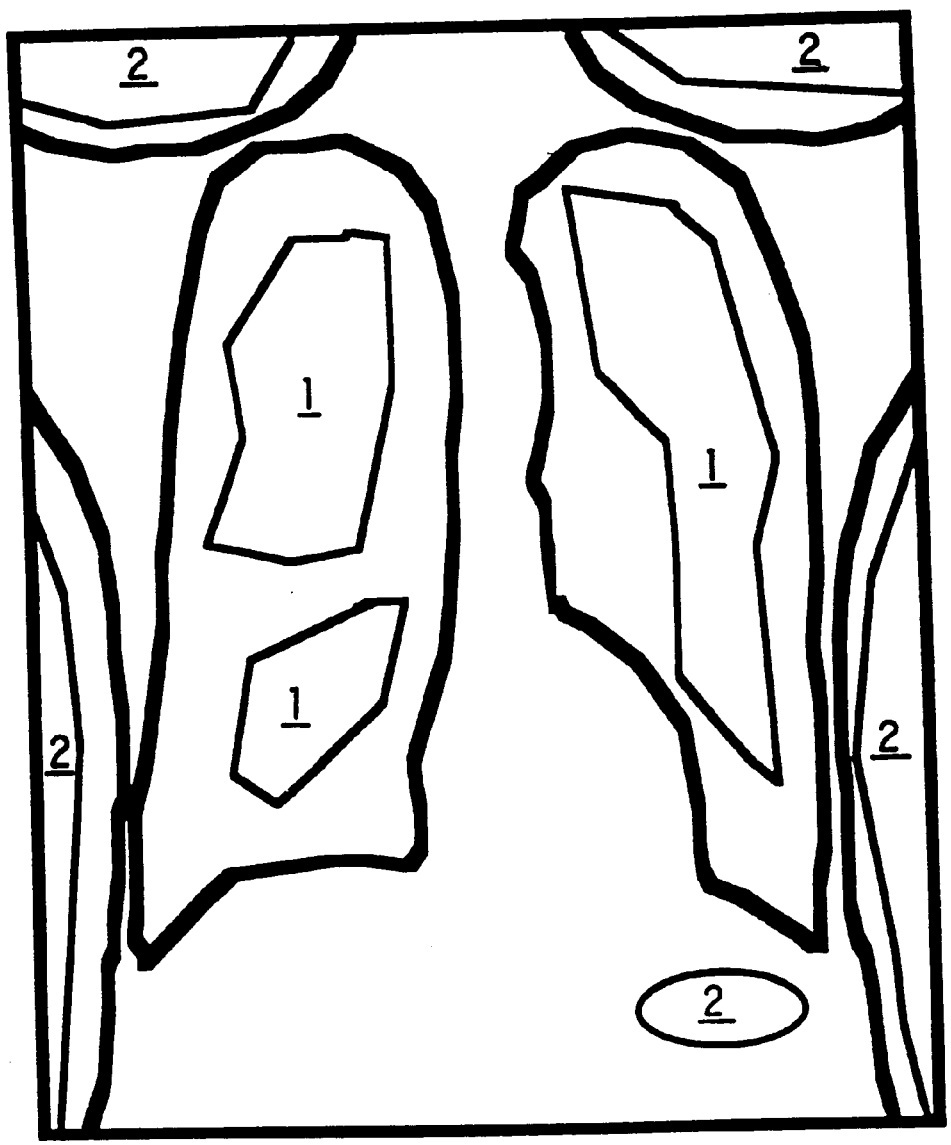
FIG. 6 is an illustration of a chest image demonstrating contours detected during an intermediate iteration, with contours labeled 1 passing the centroid check and contours labeled 2 failing the centroid check.
Figure 7A:
FIGS. 7(a) and 7(b) are photographs/illustrations of binary images demonstrating the effect of the centroid check (FIG. 7(a)) and the morphological open operation (FIG. 7(b))

To prevent merging, in substep S505 a centroid check is performed for each contour constructed at each iteration. See Armato et al., "Automated Lung Segmentation in Digital Posterior Chest Radiographs," Academic Radiology (in press), which is incorporated by reference herein. A horizontal gray-level profile is obtained through the image pixel representing the contour's centroid, extending from the midline column to the corresponding edge of the image. The positions and gray-levels of maxima and minima relative to the position and gray-level of the centroid pixel are used to assess whether the contour encompasses a region of the lungs. Depending on the location of the centroid, a vertical gray-level profile beginning at the centroid and extending to the top or bottom of the image is also analyzed to provide additional information about the region included within the contour. If the centroid check indicates that the contour exists outside the lung field, in substep 506 all image pixels enclosed by the contour are prohibited from contributing to the binary images (and hence the contours) created at later iterations. FIG. 6 shows a chest image demonstrating contours detected during an intermediate iteration. Contours labeled 1 pass the centroid check. Contours labeled 2 fail the centroid check. Accordingly, pixels within these latter contours are prevented from being turned "on" during subsequent iterations. These external regions are thus prevented from merging with regions within the lungs at later iterations where the threshold gray-level is greater and the likelihood of such a merge is increased. Lung contours resulting from the higher threshold values utilized during later iterations are thus able to extend more toward the lung periphery without the risk of contours that would otherwise encompass non-lung fields "leaking through" the lung boundary to combine with the lung contour. This situation would typically occur along portions of the lung boundary that are more radiolucent such as the inferior lateral margins of the ribcage and the left hemidiaphragm in the presence of bowel gas. FIGS. 5(b) and 7(a) show the binary images that result when the centroid check is not and is implemented, respectively. The binary image of FIG. 7(a) is analogous to the binary image shown in FIG. 5(b) except that a centroid check has been performed during previous iterations.

The process of thresholding to create a binary image, identifying contours, and suppressing pixels based on a centroid check is repeated for each of the seven iterations, with the threshold values used to produce the binary images increasing at each iteration. A morphological open operation

Figure 7B:
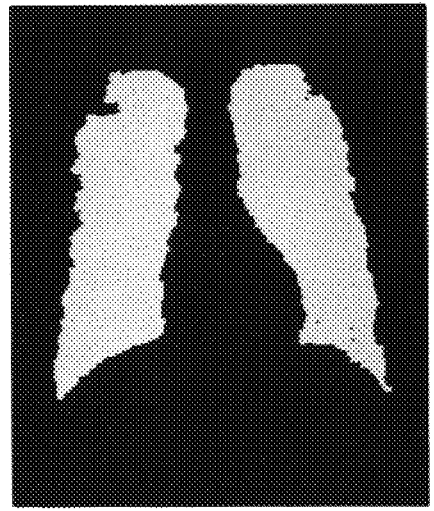

[37] with a 3×3-pixel kernel is applied to the binary images during each of the final three iterations. FIG. 7(b) shows the result of performing a morphological open operation on the binary image of FIG. 7(a) to remove slender artifacts. This combination of an erosion operation followed by a dilation operation eliminates many of the slender artifacts that remain "on" in the binary image as a result of the process that suppresses regions of the image based on the centroid check. The end result of the global gray-level thresholding scheme is an initial set of contours representing the aerated lung fields in the image.

Since the initial contours tend to appear somewhat irregular, a smoothing scheme is applied that utilizes a running mean algorithm. This substitutes for the x- and y-positions of each contour point the average x- and y-positions of nine preceding and nine succeeding contour points. In addition, points that are redundant in an eight-point connectivity sense are eliminated from the contours.

Figure 8A:
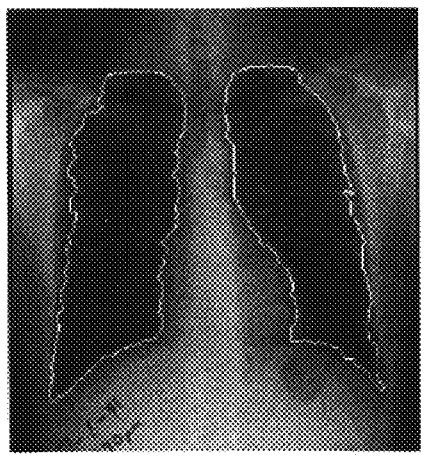
FIGS. 8(a) and 8(b) are photographs/illustrations of the initial set of lung contours resulting from iterative global gray-level thresholding before (FIG. 8(a)) and after (FIG. 8(b)) smoothing for the image shown in FIG. 2.
Figure 8B:
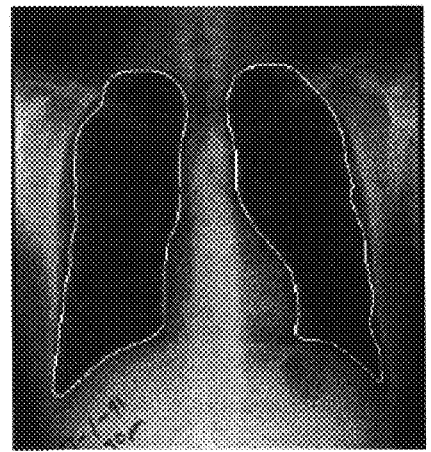

FIG. 8(a) shows an initial set of lung contours resulting from iterative global gray-level thresholding for the image shown in FIG. 2. FIG. 8(b) shows the result of smoothing the contours of FIG. 8(a).

Figure 9A:
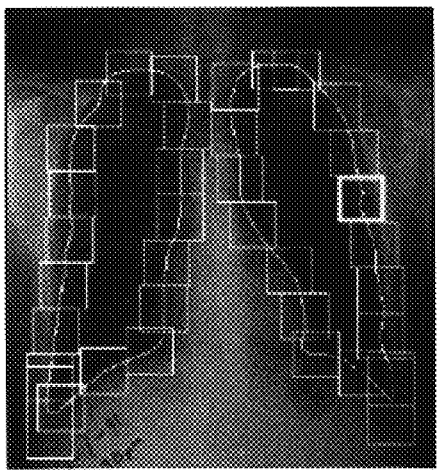
FIGS. 9(a), 9(b) and 9(c) are photographs/illustrations which demonstrate the local gray-level thresholding technique showing ROI placement along the smoothed initial contours with the gray-level histogram (FIG. 9(c))of the bolded ROI indicating its selected threshold (FIG. 9(a)) and the composite binary image created by thresholding pixels within individual ROIs (FIG. 9(b))

The initial contours based on global gray-level thresholding tend to under-represent the actual aerated lung fields shown in FIG. 8(b). To rectify this situation, in step S6 a local gray-level thresholding scheme is applied to the output of the global thresholding scheme of step S5. Overlapping ROIs with dimension 31×31 pixels are centered at every 30th pixel along the initial contours. The ROI dimensions required to adequately perform local thresholding depend on the degree to which the contours resulting from global thresholding approximate the actual lung borders. We selected a single ROI size (31×31 pixels) based on empirical observations of the initial contours. FIG. 9(a) demonstrates ROI placement along the smoothed initial contours of FIG. 8(b).

Although all initial contours are retained, local thresholding is performed only on the two largest contours in the image, and then only if these contours occupy different hemithoraces. ROIs are assigned one of two location categories (medial or lateral) as they are placed along the initial contours in a counterclockwise manner, beginning with the superiormost point of each contour.

Figure 9B:
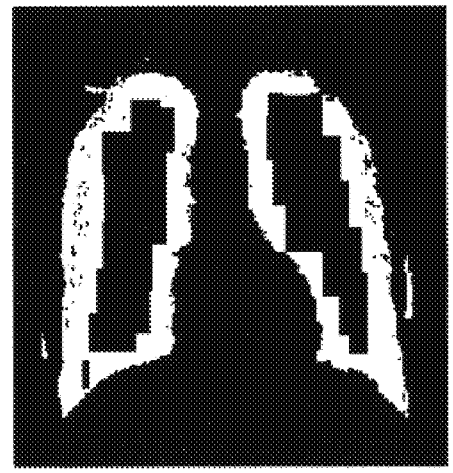
Figure 9C:
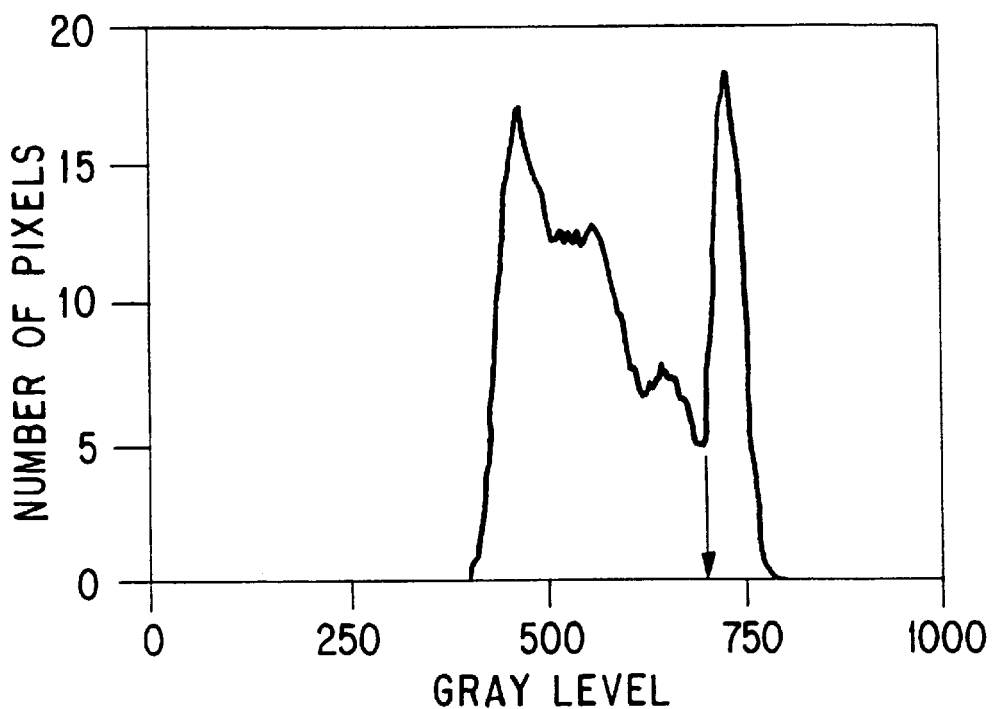
Figure 10:
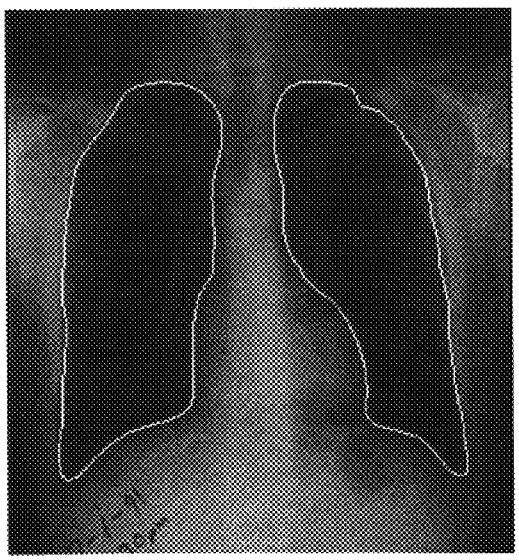
FIG. 10 is a photograph/illustration which depicts a set of lung contours for the image shown in FIG. 9(a) after local thresholding and smoothing.

Gray-level analysis is performed on pixels within each ROI, and a gray-level threshold is determined separately for the individual ROIs based on their location categories. The threshold for a medial ROI is defined as the mean gray-level of pixels within the ROI. For a lateral ROI, a gray-level histogram (FIG. 9(c)) is constructed from all pixels within the ROI (FIG. 9(a)), and the initial threshold is set to the gray-level at which the minimum with the largest gray-level occurs (i.e., the rightmost minimum in the histogram, excluding the endpoint) as indicated by the arrow in FIG. 9(c). The threshold actually used for a lateral ROI is the average of its initial threshold and that of the two adjacent ROIs. A composite binary image is then created by thresholding the pixels in each ROI based on the threshold value selected for that ROI such that a pixel is turned "on" in the binary image if its corresponding image pixel has a gray-level less than the chosen threshold. FIG. 9(b) shows the composite binary image created by thresholding pixels within the individual ROIs. The contour detection scheme is applied to the composite binary image to construct the final contours, which are then smoothed in step S7 in the same manner as the initial contours previously discussed. FIG. 10 shows the resulting lung contours for the image of FIG. 9(a) after local thresholding and smoothing is applied.

Large-scale aberrations are sometimes present in the final contours, appearing as depressions or protrusions. These typically occur in the apex region, where a dense clavicle may cause the contour to bow inwards in order to exclude the highest-gray-level portion of the clavicle (thus forming a depression in the contour), or a relatively radiolucent region of the shoulder may erroneously be captured by the contour, causing it to extend outwards (forming a protrusion). In step S8 a rolling ball algorithm is adapted from Sternberg to address this problem. The rolling ball presented by Sternberg is a spherical structuring element used to process images through gray scale opening and closing operations [40]. A ball is conceptually rolled along the three-dimensional surface representing gray-level as a function of spatial position in the image; filtering occurs where depressions exist in this surface that are sharp enough to prevent the ball of a specified radius to remain in contact with the surface. The rolling ball we define analogously rolls along the two-dimensional curve defined by a lung contour. Depressions are identified where the rolling ball is unable to remain in contact with the contour.

Figure 11:
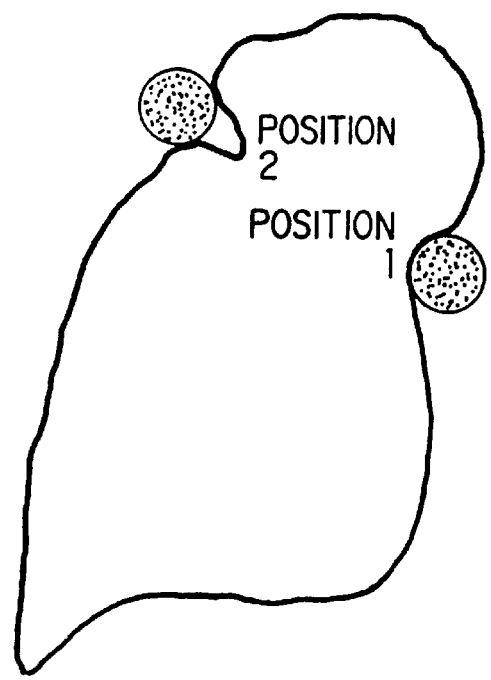
FIG. 11 is an illustration for describing the rolling ball algorithm for identifying depressions in a contour, with the indentation at Position 1 not deep enough to qualify as a depression, while Position 2 is considered a depression.

FIG. 11 is an illustration of the rolling ball algorithm for identifying depressions in a contour. The indentation at Position 1 is not deep enough to qualify as a depression, while Position 2 is considered a depression, because it prevents the ball from remaining in contact with the contour. Applying the algorithm to the external side of the contour eliminates depressions, while applying it to the internal side eliminates protrusions.

A circular filter (the "ball") is constructed with radius 13 pixels for internal application or 25 pixels for external application. These radii were chosen to match the observed size of protrusions and depressions that tend to be present along the contours. The ball is "rolled" along the contour by successively identifying that pixel along the ball's circumference with a tangential slope that matches the slope of the current contour point; the filter is then positioned to align the selected ball circumference pixel with the contour pixel. If a depression of the proper scale is encountered, the ball will overlap the contour at some contour point other than the point of contact used to place the filter as shown by Position 2 in FIG. 11. This overlap point along with the point of contact define endpoints of the depression. Linear interpolation is then employed to create new contour points that connect the depression endpoints, effectively bridging the gap in the contour and eliminating the depression.

Figure 12:
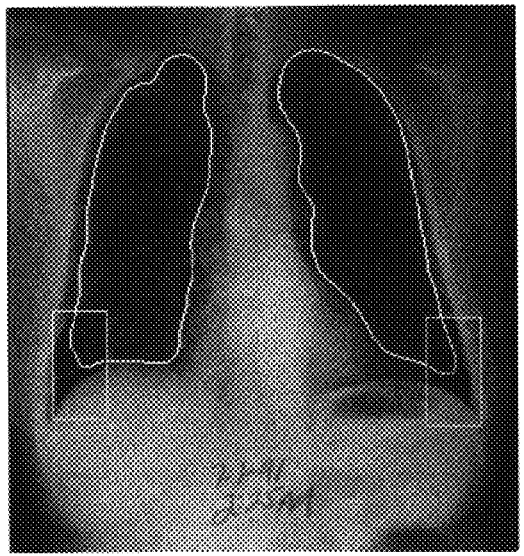
FIG. 12 is a photograph/illustration which depicts the lung segmentation contours resulting from iterative global gray-level thresholding and demonstrates the placement of the CP angle ROIs during local gray-level thresholding.

The contours produced in this manner tend to under-represent the costophrenic angles. To accommodate this important anatomic feature, first stage CP angle ROI placement is performed as part of the local thresholding process. During first stage CP angle ROI placement, a vertically oriented ROI (31×61 pixels) is placed over the initial contour point with the greatest distance from the opposite upper corner of the image. The ROI placed in this manner is presumed to encompass the actual CP angle. However, in some cases, the initial segmentation contours under-represent the lung to such an extent that this ROI fails to encompass the CP angle at this step. The average gray-level of the pixels within this ROI is defined as the threshold, which is then used to create another portion of the composite binary image. This is performed for each hemithorax. FIG. 12 shows the result of first stage ROI placement on the lung segmentation contours resulting from global threshold analysis. The shaded pixels represent those that will contribute to the composite binary image, which is used to construct the final lung segmentation contours.

Figure 13:
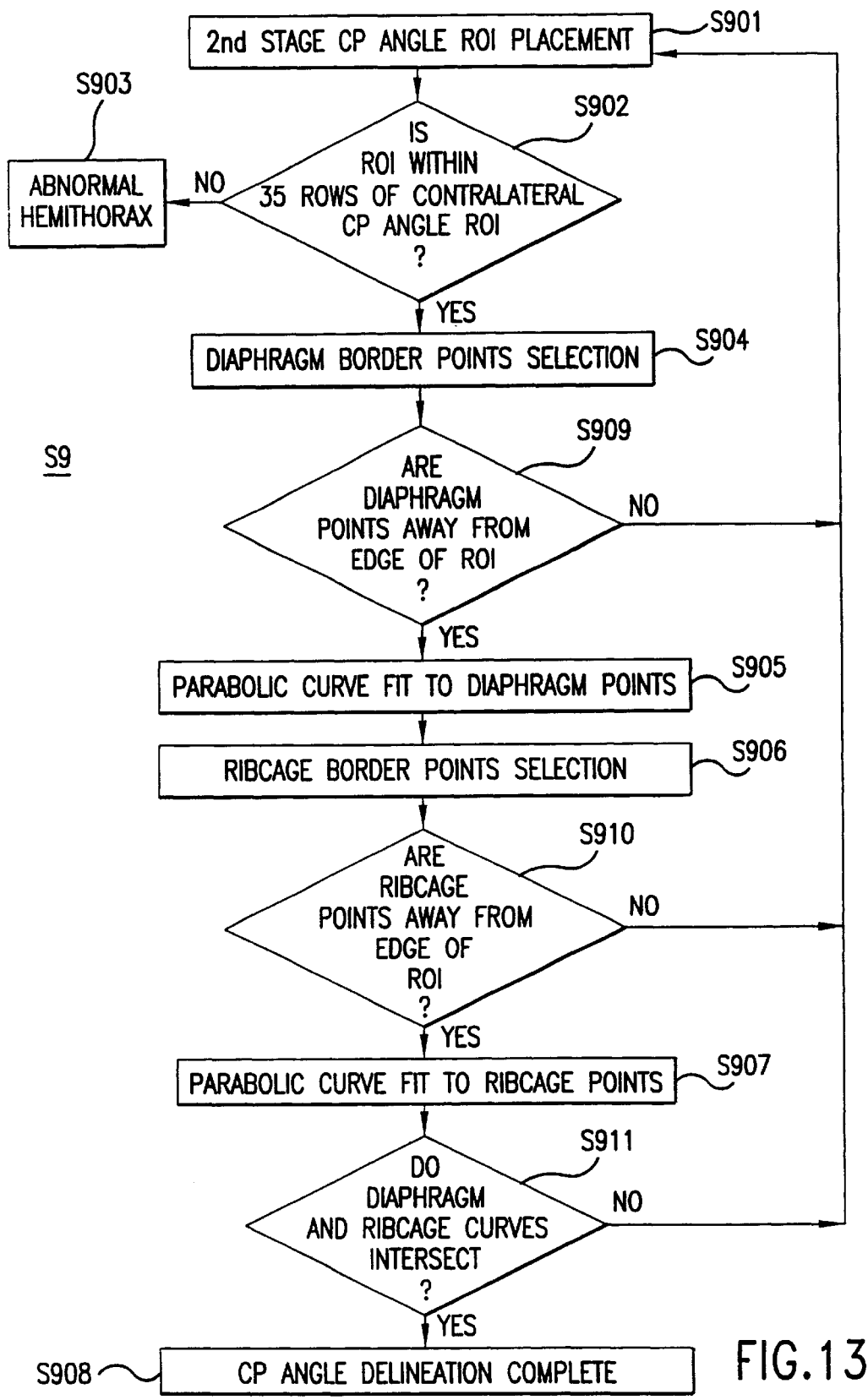
FIG. 13 is a flowchart showing the substeps performed during CP angle delineation.

Referring back to FIG. 1, in step S9 costophrenic angle delineation is performed to extend the lung segmentation contours closer to the actual CP angle border. As shown by the flowchart of FIG. 13, step S9 is inclusive of substeps S901 through S911.

Figure 14:
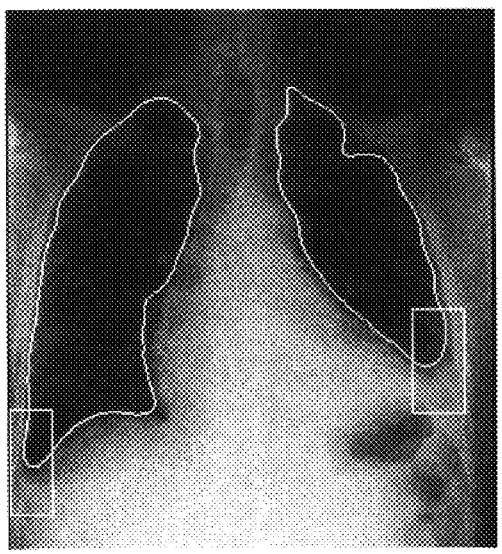
FIG. 14 is a photograph/illustration of a PA chest image demonstrating severe pleural effusion in the left hemithorax with placement of the second-stage CP angle ROIs indicating a difference in vertical position between the ROIs sufficient to classify the left CP angle as abnormal without subsequent delineation.

In substep S901 second stage CP angle ROI placement is performed by placing ROIs on the smoothed contours resulting from local threshold analysis. For each lung segmentation contour, a 31×61-pixel ROI is placed with its center at the new contour pixel most distant from the contralateral upper corner of the image. Then, in substep S902 the relative positions of the second-stage CP angle ROIs for right and left lung segmentation contours are compared. If the vertical position of either CP angle ROI lies superior to that of the other ROI by 35 rows or more, second-stage analysis is not performed for the more superior ROI. Such a discrepancy in position is presumed to result from an abnormality in the lung base that reduces the aerated lung volume, thereby causing the lung segmentation scheme to exclude the base. FIG. 14 shows a PA chest image demonstrating severe pleural effusion in the left hemithorax with placement of the second-stage CP angle ROIs indicating a difference in vertical position between the ROIs sufficient to classify the left CP angle as abnormal without subsequent delineation. This type of abnormality would typically render the CP angle imperceptible and an attempted delineation meaningless. For these cases, the CP angle is labeled abnormal in substep S903, and the delineation procedure is terminated.

Figure 15:
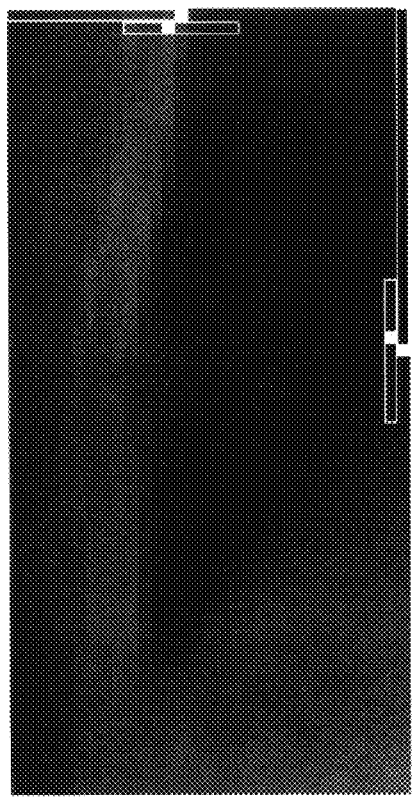
FIG. 15 is a photograph/illustration which depicts the CP angle subimage extracted from the right hemithorax of a normal PA chest image, with the locations of the first (most medial) diaphragm point and first (most superior) costal point shown along with the search regions used to locate the corresponding second points.
Figure 16A:
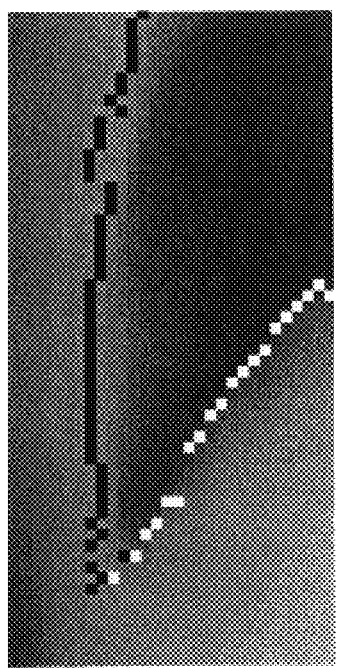
FIGS. 16(a) and 16(b) are photographs/illustrations which depict the CP angle subimage demonstrating initial diaphragm and costal points (FIG. 16(a)) and the least-squares parabolas fit to the initial points (FIG. 16(b))
Figure 16B:
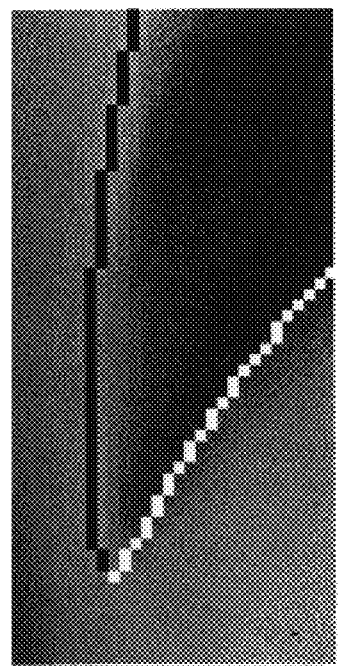

The subimage defined by each CP angle ROI is then further analyzed. In substep S904 the diaphragm border is delineated. The highest contrast pixel in the medial-most column of this subimage is identified as the first diaphragm point, where contrast is defined as the difference between gray-levels of the pixels immediately below and above the current pixel divided by the gray-level of the current pixel. Eleven consecutive pixels in the adjacent column form a search region for the next diaphragm point. These pixels extend from four rows above the row of the first diaphragm point to six rows below it; the downward trend of the diaphragmatic border as it courses laterally justifies this asymmetry. The pixel at which the largest gray-level difference between neighboring pixels occurs is identified as the next diaphragm point. FIG. 15 is a CP angle subimage extracted from the right hemithorax of a normal PA chest image. The locations of the first (most medial) diaphragm point and first (most superior) costal point are shown along with the search regions used to locate the corresponding second points. This process continues for subsequent columns in the subimage until a complete set of diaphragm points is obtained. Columns cease contributing diaphragm points when an upward trend in the diaphragm points is detected; such a trend occurs when columns outside the lung field are examined. A similar trend could result from pathology in the CP angle, in which case elimination of these diaphragm points would be incorrect; however, the costal delineation tends to compensate for this omission. FIG. 16(a) shows a CP angle subimage with initial diaphragm points denoted by bright pixels. In substep S905 a least-squares parabola is calculated to define a continuous curve that best fits these diaphragm points as shown. This curve delineates the diaphragmatic margin of the CP angle. FIG. 16(b) shows the result (in bright pixels) of a least-squares parabola fit to the initial diaphragm points of FIG. 16(a).

Next, in substep S906 the costal border is delineated. The first costal point is identified as the maximum-gray-level pixel in the top row of the subimage. The search region in the adjacent row consists of nine consecutive pixels, which are symmetrically positioned about the column containing the first costal point as shown in FIG. 15. The next costal point is chosen from among these nine as the one with maximum gray-level. Selection of costal points in subsequent rows continues in this manner until a costal point that lies inferior to the diaphragm curve is identified. FIG. 16(a) shows a CP angle subimage with initial costal points denoted by dark pixels. Then, in substep S907 a least-squares parabola is used to fit a continuous curve through these costal points, thus delineating the costal margin of the CP angle. FIG. 16(b) shows the result (in dark pixels) of a least-squares parabola fit to the initial costal points of FIG. 16(a). The diaphragmatic and costal margins are truncated at (or extended to) their point of intersection to form a single, continuous curve within the subimage. It remains for this curve to be properly integrated with the final lung segmentation contour as a whole. Furthermore, once delineation is complete in substep S908, quantitative analysis of the angle subtended by the diaphragmatic and costal margins of the CP angle is performed to assess the presence of an abnormality.

Figure 17A:
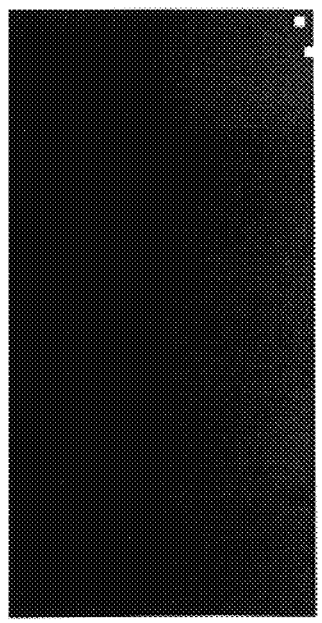
FIGS. 17(a) and 17(b) are photographs/illustrations which depict "diaphragm points" along the top rows of the subimage indicating the ROI is too inferior (FIG. 17(a)) and "costal points" along the edge of the subimage indicating the ROI is too medial (FIG. 17(b))
Figure 17B:
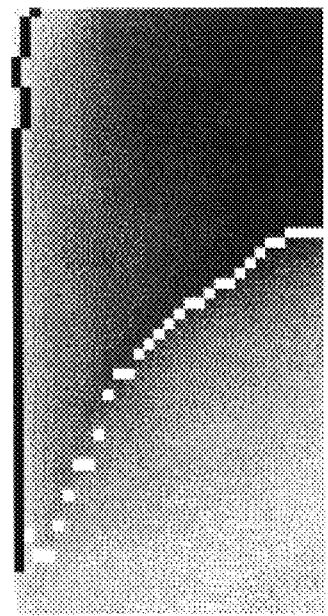

A number of checks are implemented during the CP angle delineation procedure to assess the accuracy of ROI placement. In substep S909 if it is determined that pixels identified as diaphragm points are located in the top two rows of the subimage, the CP angle ROI is considered too inferior as shown in the image of FIG. 17(a); accordingly, the ROI is moved superiorly, and the process returns to substep S901 so that CP angle delineation is repeated. Similarly, in substep S910 if it is determined that pixels identified as costal points are located along the lateral edge of the subimage, the ROI is too medial and must be moved laterally as shown in FIG. 17(b). Moreover, if in substep S911 it is determined that the diaphragm and costal curves fail to intersect in the ROI, then the ROI is moved to include the intersection. Several iterations of ROI repositioning may occur before the ROI is determined to include the CP angle.

Referring back to FIG. 1, once the CP angles have been delineated, in step S10 they are integrated with the overall lung segmentation to form a continuous contour. This is achieved using linear interpolation to connect costal and diaphragmatic splice points identified through a slope-matching technique. For the costal aspect of each CP angle margin, the slope at the superiormost delineation point is calculated. The slope of successive points along the corresponding lung contour is then examined starting with the contour point closest to the top row of the subimage region. The appropriate splice point in the lung contour has the same slope as the superiormost costal delineation point, which is the other splice point. Linear interpolation is used to connect these two splice points. The same process is applied to the diaphragmatic margin.

Figure 18B:
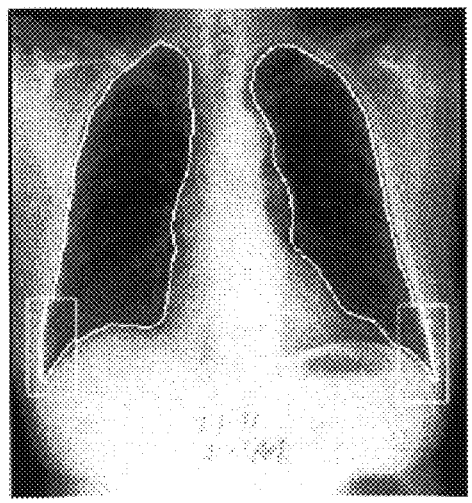
FIGS. 18(a) and 18(b) are photographs/illustrations which demonstrate incorporation of CP angle delineations into the final lung segmentation contours.
Figure 18A:
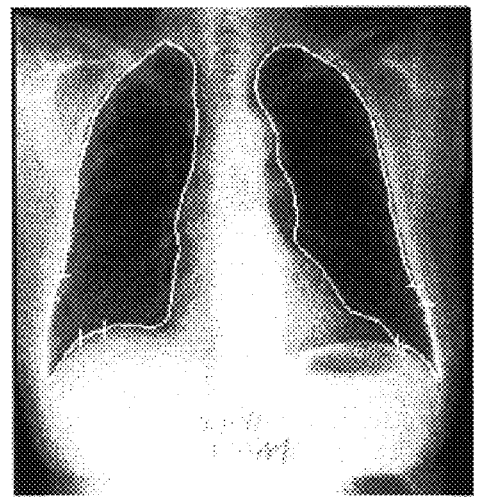

FIGS. 18(a) and 18(b) show the results of incorporating CP angle delineations into final lung segmentation contours. In FIG. 18(a) the subimages containing CP angle delineations replace the corresponding regions in the chest image of FIG. 12. In FIG. 18(b) CP angle delineations are shown integrated with the lung contours as a result of using linear interpolation to connect splice points (indicated by the hash marks).

Figure 19:
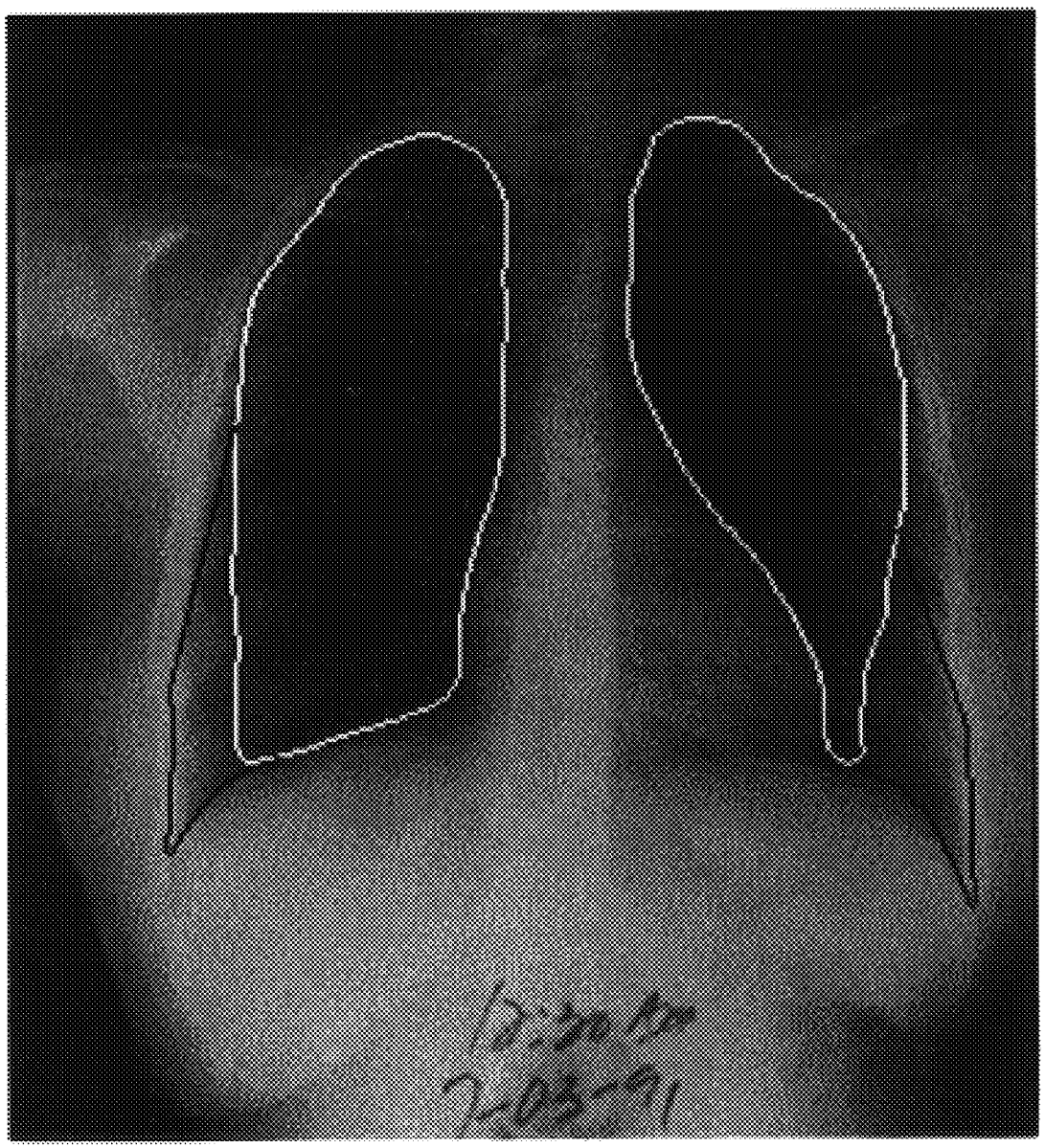
FIG. 19 is a photograph/illustration which demonstrates the ability of the CP angle delineation to rectify the final contours which would otherwise fail to adequately capture the aerated region of the right hemithorax.

This process, along with the ROI position verification procedure previously discussed, allows a lung segmentation contour that inadequately captures the lung field to be effectively extended to include the CP angle, thereby reducing the area of aerated lung omitted from the segmentation contour. FIG. 19 shows the lung segmentation contours (in white) prior to CP angle delineation for a normal image. These fail to adequately capture the aerated region of both lungs. The contour segments shown in black serve to rectify the final contours after CP delineation and splicing are performed. Lung segmentation is now complete.

Figure 20:
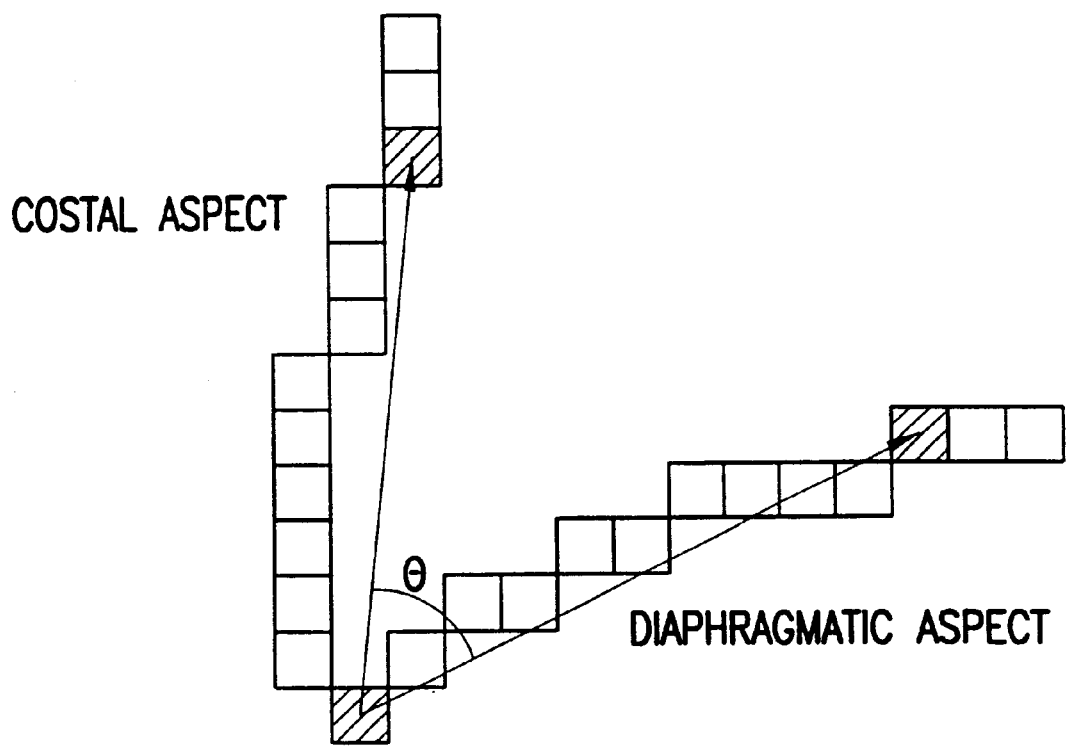
FIG. 20 is an illustration of the CP angle delineation points used to compute the angle measure associated with each CP angle.
Figure 21:
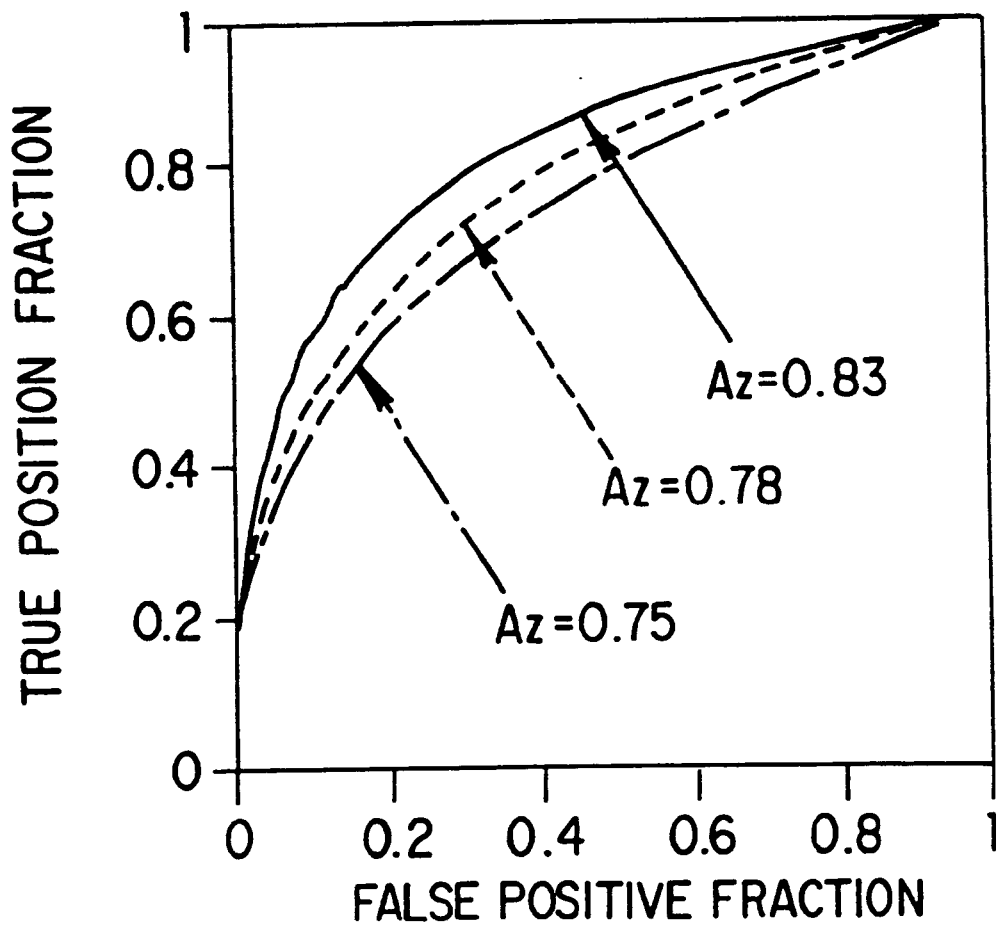
FIG. 21 is a graph of ROC curves for abnormal CP angle detection using 1166 completely imaged CP angles.

The quantifiable angle subtended by the convergence of the costal and diaphragmatic curves forming the CP angle delineation may be used to evaluate the presence of CP angle blunting or obscuration: a blunt CP angle as demonstrated on the image should yield an angle measure greater than the angle measure of a normal CP angle. The point of intersection between the costal and diaphragmatic aspects of the CP angle delineation is identified as a vertex that together with the tenth point from the vertex along each of the two delineation aspects defines the computer-extracted angle measure. FIG. 20 illustrates the CP angle delineation points used to compute the angle measure associated with each CP angle. The CP angles in a 600-image database were separately analyzed quantitatively by the computer and qualitatively by a radiologist. Both hemithoraces of each image were separately evaluated by a radiologist using a 4-point rating scale for the degree of CP angle blunting (O=normal, I=slightly blunt or obscure, 2=intermediate blunting, 3=severely blunt or obscure). Receiver operating characteristic (ROC) analysis [41] was performed using the calculated angle of the computer-determined CP angle delineations as the decision variable. Each CP angle was evaluated individually based on its own angle measure in relation to the rating assigned by the radiologist. The resulting ROC curves are shown in FIG. 21. The curves are based on 1166 usable CP angles, which excludes 34 CP angles (of the 1200 total in the database) that were not completely imaged due to improper patient positioning. Although the automated segmentation scheme can accommodate this situation, the calculated values for such cut-off CP angles are without physical meaning. As previously discussed, CP angle delineation is not performed in a hemithorax if the CP angle ROI in that hemithorax is 35 rows or more superior to the CP angle ROI in the contralateral lung, since we assume that such a hemithorax is abnormal to the extent that attempted CP angle delineation would be meaningless. Consequently, these CP angles are assigned an artificial value of 180 degrees for the purpose of automated quantitative analysis. The median computer-determined angle measures for CP angles assigned a radiologist rating of 0 (normal), 1 (slightly blunt), 2 (intermediate blunting), or 3 (severe blunting) were 42.4 degrees, 57.2 degrees, 57.9 degrees, and 90.0 degrees, respectively.

FIG. 21 shows three ROC curves, which differ with respect to the criterion for considering an angle "truly" abnormal. When the strictest definition of abnormal is applied (i.e., only CP angles with a radiologist assessment rating of 3), $A_z$=O0.83±0.031. With abnormal defined by a rating of 2 or 3, the $A_z$ value is 0.78±0.027. Lastly, with abnormal defined by a radiologist assessment rating of 1, 2, or 3, the $A_z$ value is 0.75±0.023. All $A_z$ values were obtained using the LABROC4 software package [42].

This invention may be conveniently implemented using a conventional general purpose digital computer or microprocessor programmed according to the teachings of the present specification, as will be apparent to those skilled in the computer art. Appropriate software coding can readily be prepared by skilled programmers based on the teachings of the present disclosure, as will be apparent to those skilled in the software art.

The present invention includes a computer program product which is a storage medium including instructions which can be used to program a computer to perform a process of the invention. The storage medium can include, but is not limited to, any type of disk including floppy disks, optical discs, CD-ROMs, and magneto-optical disks, ROMs, RAMs, EPROMs, EEPROMs, magnetic or optical cards, or any type of media suitable for storing electronic instructions.

Figure 22:
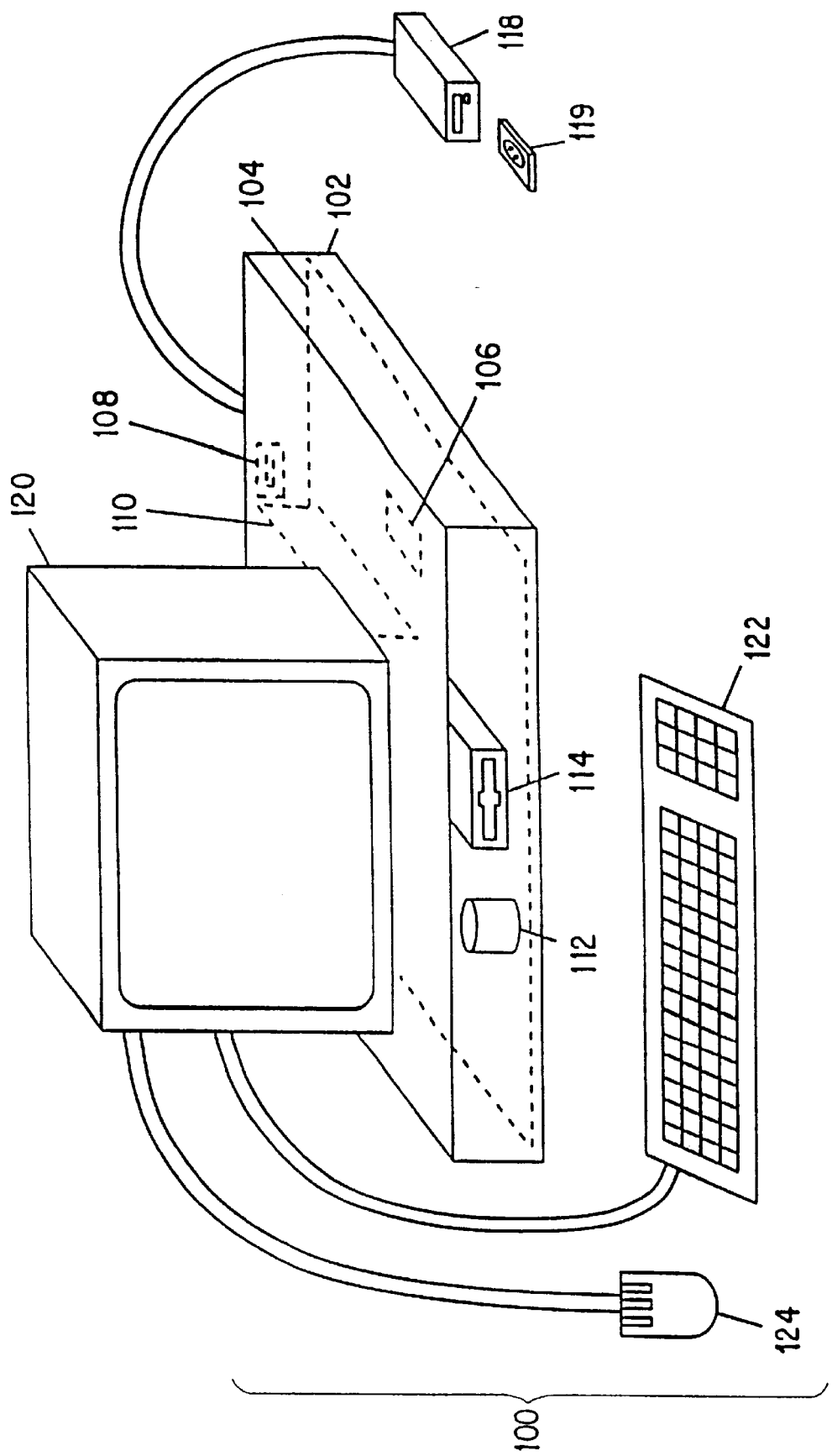
FIG. 22 is a schematic illustration of a general purpose computer 100 programmed according to the teachings of the present invention.

FIG. 22 is a schematic illustration of a general purpose computer 100 programmed according to the teachings of the present invention. The general purpose computer 100 includes a computer housing 102 having a motherboard 104 which contains a CPU 106 and memory 108. The computer 100 also includes plural input devices, e.g., a keyboard 122 and mouse 124, and a display card 110 for controlling monitor 120. In addition, the computer system 100 further includes a floppy disk drive 114 and other removable media devices (e.g., tape, and removable magneto-optical media (not shown)), a hard disk 112, or other fixed, high density media drives, connected using an appropriate device bus, e.g., a SCSI bus or an Enhanced IDE bus. Also connected to the same device bus or another device bus, the computer 100 may additionally include a compact disc reader/writer 118 or a compact disc jukebox (not shown).

Stored on any one of the above described storage medium (computer readable media), the present invention includes programming for controlling both the hardware of the computer 100 and for enabling the computer 100 to interact with a human user. Such programming may include, but is not limited to, software for implementation of device drivers, operating systems, and user applications. Such computer readable media further includes programming or software instructions to direct the general purpose computer 100 to perform tasks in accordance with the present invention.

The programming of general purpose computer 100 includes, but is not limited to, software modules for digitizing and storing PA radiographs obtained from an image acquisition device, determining the lung apex and midline, performing gray-level histogram analysis, applying a Sobel filter, performing iterative global gray-level thresholding, performing local gray-level thresholding, performing contour smoothing, applying a rolling ball filter, identifying costophrenic angles in an appropriate subimage, splicing subimage contours, superimposing lung segmentation results onto images, storing the lung segmentation results in file format, or providing the lung segmentation results in text format. Utilizing the above software modules, the programming of general purpose computer 100 also includes high level software modules that perform automated segmentation of the lung field in chest images, delineation and quantitative analysis of costophrenic angles in chest images, and integration of delineated costophrenic angles with lung fields.

The invention may also be implemented by the preparation of application specific integrated circuits or by interconnecting an appropriate network of conventional component circuits, as will be readily apparent to those skilled in the art.

Figure 23:
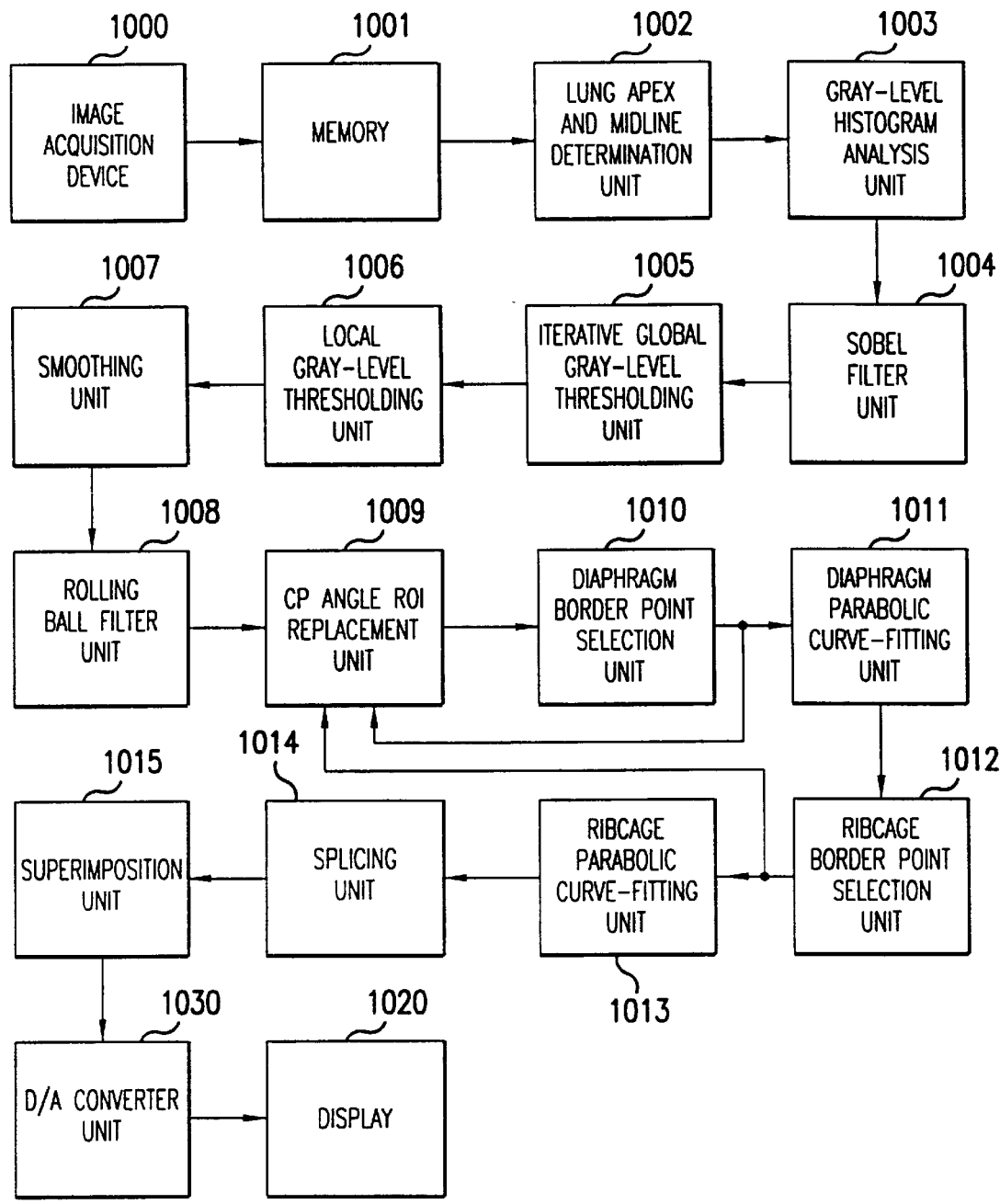
FIG. 23 is a block diagram of a system for implementing the method of the invention for the segmentation of lung fields in PA chest radiographs and the delineation of CP angles in PA chest radiographs.

FIG. 23 is a block diagram of a system for implementing the method of the invention for the segmentation of lung fields in PA chest radiographs and the delineation of CP angles in PA chest radiographs. PA radiographs of an object are obtained from an image acquisition device and input to the system 1000. Each image is digitized and put into memory 1001. If the image is obtained with a direct digital device then there is no need for digitization. The image data is first passed through the lung apex and midline determination unit 1002, and then to the gray-level histogram analysis unit 1003 and also to the Sobel filter unit 1004. The data are passed through to the iterative global gray-level thresholding unit 1005. Contour data from the iterative global gray-level thresholding circuit are passed to the local gray-level thresholding unit 1006. Contour data from the local gray-level thresholding circuit are then passed to the smoothing unit 1007 and to the rolling ball filter unit 1008. Contour data are then passed to the CP angle ROI placement unit 1009 to identify appropriate subimages. The subimages data are sent to the diaphragm border point selection unit 1010 and the diaphragm parabolic curve-fitting unit 1011. The subimage data and diaphragm contour data are then sent to the ribcage border point selection unit 1012 and the ribcage parabolic curve-fitting unit 1013. The diaphragm border point selection unit 1010 and the ribcage border point selection unit 1012 provide feedback data to the CP angle ROI placement unit 1009. The diaphragm and ribcage delineation data is then passed to the splicing unit 1014. In the superimposing unit 1015 the results are either superimposed onto images, stored in file format, or given in text format. The results are then displayed on the display 1020 after passing through a digital-to-analog converter 1030.

Obviously, numerous modifications and variations of the present invention are possible in light of the above teachings. It is therefore to be understood that within the scope of the appended claims, the invention may be practiced otherwise than as specifically described herein.

Appendix

[1] H. MacMahon and K. Doi, "Digital chest radiography," Clin. Chest Med. 12, 19–32 (1991).

[2] H. Yoshimura, X. -W. Xu, K. Doi, H. MacMahon, K. R. Hoffmann, M. L. Giger, and S. M. Montner, "Development of a high quality film duplication system using a laser digitizer: comparison with computed radiography," Med. Phys. 20, 51–58 (1993).

[3] K. R. Hoffmann, K. Doi, H. MacMahon, M. L. Giger, R. M. Nishikawa, X.-W. Xu, L. Yao, A. Kano, and M. Carlin, "Development of a digital duplication system for portable chest radiographs," J. Digital Imaging 7, 146–153 (1994).

[4] H. K. Huang and R. K. Taira, "Infrastructure design of a picture archiving and communication system," AJR 158, 743–749 (1992).

[5] M. L. Giger and H. MacMahon, "Image processing and computer-aided diagnosis," Radiol Clin North Am 34, 565–596 (1996).

[6] J. Toriwaki, Y. Suenaga, T. Negoro, and T. Fukumara. "Pattern recognition of chest x-ray images," Comput. Grap. Image Proc. 2, 252–271 (1973).

[7] M. Hashimoto, P. V. Sankar, and J. Sklansky, "Detecting the edges of lung tumors by classification techniques," Proc. IEEE Int. Conf. Patt. Recogn. 1801, 276–279 (1982).

[8] W. A. Lampeter and J. C. Wandtke, "Computerized search of chest radiographs for nodules," Invest. Radiol. 21, 384–390 (1986).

[9] M. L. Giger, K. Doi, and H. MacMahon, "Image feature analysis and compute-raided diagnosis in digital radiography. III. Automated detection of nodules in peripheral lung fields," Med. Phys. 15, 158–166 (1988).

[10] M. L. Giger, K. Doi, H. MacMahon, C. E. Metz, and F. F. Yin, "Pulmonary nodules: computer-aided detection in digital chest images," RadioGraphics 10, 41–51 (1990).

[11] H. Yoshimura, M. L. Giger, K. Doi, H. MacMahon, and S. M. Montner,"Computerized scheme for the detection of pulmonary nodules: a nonlinear filtering technique," Invest. Radiol. 27, 124–129 (1992).

[12] S. Katsuragawa, K. Doi, and H. MacMahon, "Image feature analysis and computer-aided diagnosis in digital radiography: detection and characterization of interstitial lung disease in digital chest radiographs," Med. Phys. 15, 311–319 (1988).

[13] S. Katsuragawa, K. Doi, and H. MacMahon, "Image feature analysis and computer-aided diagnosis in digital radiography: classification of normal and abnormal lungs with interstitial disease in chest images." Med. Phys. 16, 38–44 (1989).

[14] S. Katsuragawa, K. Doi, H. MacMahon, N. Nakamori, Y. Sasaki, and J. J. Fennessy, "Quantitative computer-aided analysis of lung texture in chest radiographs," Radiographic 10, 257–269 (1990).

[15] S. Sanada. K. Doi, and H. MacMahon, "Image feature analysis and computer-aided diagnosis in digital radiography: automated detection of pneumothorax in chest images," Med. Phys. 19, 1153–1160 (1992).

[16] R. P. Kruger, J. R. Townes, D. L. Hall, S. J. Dwyer, III, and G. S. Lodwick, "Automated radiographic diagnosis via feature extraction and classification of cardiac size and shape descriptors," IEEE Trans. Biomed. Eng. 19, 174–186 (1972).

[17] N. Nakamori, K. Doi, V. Sabeti, and H. MacMahon, "Image feature analysis and computer-aided diagnosis in digital radiography: automated analysis of sizes of heart and lung in chest images," Med. Phys. 17, 342–350 (1990).

[18] A. Kano, K. Doi, H. MacMahon, D. D. Hassell, and M. L. Giger, "Digital image subtraction of temporally sequential chest images for detection of interval change," Med. Phys. 21, 453–461 (1994).

[19] G. F. Powell, K. Doi, and S. Katsuragawa, "Localization of inter-rib spaces for lung texture analysis and computer-aided diagnosis in digital chest images," Med. Phys. 15, 581–587 (1988).

[20] H. Wechsler and J. Sklansky, "Finding the rib cage in chest radiographs," Pattern Recog. 9, 21–30 (1977).

[21] S. Sanada, K. Doi, and H. MacMahon, "Image feature analysis and computer-aided diagnosis in digital radiography: automated delineation of posterior ribs in chest images," Med. Phys. 18, 964–971 (1991).

[22] X. Chen, K. Doi, S. Katsuragawa, and H. MacMahon, "Automated selection of regions of interest for quantitative analysis of lung textures in digital chest radiographs," Med. Phys. 20, 975–982 (1993).

[23] X. -W. Xu and K. Doi, "Image feature analysis for computer-aided diagnosis: accurate determination of ribcage boundary in chest radiographs," Med. Phys. 22, 617–626 (1995).

[24] D. Cheng and M. Goldberg, "An algorithm for segmenting chest radiographs," Proc. SPIE 1001, 261–268 (1988).

[25] E. Pietka, "Lung segmentation in digital radiographs," J. Digital Imaging 7, 79–84 (1994).

[26] S. G. Armato, III, M. L. Giger, and H. MacMahon, "Computerized detection of abnormal asymmetry in digital chest radiographs," Med. Phys. 21, 1761–1768 (1994).

[27] J. Duryea and J. M. Boone, "A fully automated algorithm for the segmentation of lung fields on digital chest radiographic images," Med. Phys. 22, 183–191 (1995).

[28] R. H. Sherrier and G. A. Johnson, "Regionally adaptive histogram equalization of the chest," IEEE Trans. Med. Imaging MI-6, 1–7 (1987).

[29] M. I. Sezan, A. M. Tekalp, and R. Schaetzing, "Automatic anatomically selective image enhancement in digital chest radiography," IEEE Trans. Med. Imaging 8, 154–162 (1989).

[30] M. F. McNitt-Gray, H. K. Huang, and J. W. Sayre, "Feature selection in the pattern classification problem of digital chest radiograph segmentation," IEEE Trans. Med. Imaging 14, 537–547 (1995).

[31] J. C. Rudikoff, "Early detection of pleural fluid," Chest 77, 109–111 (1980).

[32] J. A. P. Pare and R. G. Fraser, *Synopsis of diseases of the chest* (W. B. Saunders Company, Philadelphia, Pa., 1983).

[33] P. E. Andersen, Jr, L. H. Andersen, and P. Jest, "The chest radiograph in chronic obstructive lung disease compared with measurements of single-breath nitrogen washout spirometry," Clin. Radiol. 33, 51–55 (1982).

[34] P. Lohela, S. Sutinen, P. Paakko, R. Lahti, and J. Tienari, "Diagnosis of emphysema on chest radiographs," Fortschr Roentgenstr 141, 395–402 (1984).

[35] R. Lilis, Y. Lerman, and I. J. Selikoff, "Symptomatic benign pleural effusions among asbestos insulation workers: residual radiographic abnormalities," Br J Indust Med 45, 443–449 (1988).

[36] S. G. Armato, III, M. L. Giger, and H. MacMahon, "Computerized delineation and analysis of costophrenic angles in digital chest radiographs," Acad. Radiol. in press

[37] J. Serra, *Image analysis and mathematical morphology* (Academic, New York, N.Y., 1982).

[38] K. T. Bae, M. L. Giger, C. -T. Chen, and C. E. Kahn, Jr., "Automatic segmentation of liver structure in CT images," Med. Phys. 20, 71–78 (1993).

[39] M. L. Giger, K. T. Bae, and H. MacMahon, "Computerized detection of pulmonary nodules in computed tomography images," Invest. Radiol. 29, 459–465 (1994).

[40] S. R. Sternberg, "Grayscale morphology," Computer Vision, Graphics, and Image Processing 35, 333–355 (1986).

[41] C. E. Metz, "ROC methodology in radiologic imaging," Invest. Radiol. 21, 720–733 (1986).

[42] C. E. Metz, B. A. Herman, and J. -H. Shen. "Maximum-likelihood estimation of receiver operating characteristic (ROC) curves from continuouslv-distributed data," Stat. Med. in press (1997).

What is claimed as new and desired to be secured by Letters Patent of the United States is:

1. A method for identifying lung fields within a chest region based on posteroanterior chest radiographic images, comprising:

generating first image data representative of a posteroanterior chest image inclusive of lung fields;

performing global threshold analysis of the posteroanterior chest image;

constructing, based on said global threshold analysis, first initial lung segmentation contours for said posteroanterior chest image;

performing, based on said first initial lung segmentation contours, local threshold analysis to construct second initial lung segmentation contours for said posteroanterior chest image; and applying a rolling ball filter to said second initial lung segmentation contours to smooth the shape of said second initial lung segmentation contours.

2. The method according to claim 1, further comprising:

performing global gray-level histogram analysis of said posteroanterior chest radiographic image to identify a maximum gray-level and a minimum gray-level designating a gray-level threshold range;

wherein said performing global threshold analysis further comprises:

a) generating a binary image having pixels having either a first logic level or a second logic level based on a gray-level threshold within said gray-level threshold range;

b) repeating substep a) a predetermined number of times at progressively larger gray-level thresholds within the gray-level threshold range; and c) processing said binary image to eliminate pixels outside the lung fields.

3. The method according to claim 1, wherein said performing local threshold analysis comprises:

positioning regions-of-interest (ROIs) along said first initial lung segmentation contours;

performing local gray-level thresholding within each of said ROIs;

generating a composite binary image based on said performing local gray-level thresholding; and constructing based on said composite binary image said second initial lung segmentation contours for said posteroanterior chest image.

4. The method according to claim 1, further comprising:

delineating costophrenic angle margins for each of said lung fields; and constructing final lung segmentation contours based on said first initial lung segmentation contours and said costophrenic angle margins.

5. The method according to claim 4, wherein said constructing final lung segmentation contours comprises:

splicing said costophrenic angle margins to said second initial lung segmentation contours to construct said final lung segmentation contours.

6. The method according to claim 4, wherein said delineating costophrenic angle margins comprises:

determining whether said posteroanterior chest image exhibits an abnormal hemithorax.

7. A method for identifying lung fields within a chest region based on posteroanterior chest radiographic images, comprising:

generating first image data representative of a posteroanterior chest image inclusive of lung fields;

performing global threshold analysis of the posteroanterior chest image;

constructing, based on said lung fields identified in said processed image global threshold analysis, first initial lung segmentation contours for said posteroanterior chest image and;

performing global gray-level histogram analysis of said posteroanterior chest radiographic image to identify a maximum gray-level and a minimum gray-level designating a gray-level threshold range;

wherein said performing global threshold analysis further comprises:

a) generating a binary image having pixels having either a first logic level or a second logic level based on a gray-level threshold within said gray-level threshold range, b) repeating substep a) a predetermined number of times at progressively larger gray-level thresholds within the gray-level threshold range, and c) processing said binary image to eliminate pixels outside the lung fields;

wherein substep c) comprises:

constructing intermediate lung segmentation contours representing boundaries of groups of contiguous pixels having said first logic level, determining the centroid for each of said intermediate lung segmentation contours;

detecting centroids outside the lung fields based on a gray-level profile, and prohibiting regions of the binary image defined by intermediate lung segmentation contours having centroids outside the lung fields from having said first logic level during subsequent iterations of substep a) generating.

8. The method according to claim 7, wherein said performing global threshold analysis further comprises:

smoothing the intermediate lung segmentation contours constructed during the last iteration of said generating a binary image to provide said first initial lung segmentation contours.

9. A method for identifying lung fields within a chest region based on posteroanterior chest radiographic images, comprising:

generating first image data representative of a posteroanterior chest image inclusive of lung fields;

performing global threshold analysis of the posteroanterior chest image;

constructing, based on said lung fields identified in said processed image global threshold analysis, first initial lung segmentation contours for said posteroanterior chest image;

delineating costophrenic angle margins for each of said lung fields; and constructing final lung segmentation contours based on said first initial lung segmentation contours and said costophrenic angle margins;

wherein said delineating costophrenic angle margins comprises:
a) placing costophrenic regions of interest (ROIs) over approximate locations of each costophrenic angle as determined based on the first initial lung segmentation contours;
b) identifying diaphragm border points within each of said ROIs;
c) identifying costal border points within each of said ROIs;
d) checking the placement of said ROIs at least once to determine whether the ROIs were positioned accurately in substep a); and
e) repeating substeps a) through d) if it is determined in substep d) that the ROIs were not accurately positioned in substep a).

10. A computer readable medium storing computer instructions for identification of lung fields within a chest region based on posteroanterior chest radiographic images, by performing the steps of:

generating first image data representative of a posteroanterior chest image inclusive of lung fields;

performing global threshold analysis of the posteroanterior chest image;

constructing, based on said global threshold analysis, first initial lung segmentation contours for said posteroanterior chest image;

performing, based on said first initial lung segmentation contours, local threshold analysis to construct second initial lung segmentation contours for said posteroanterior chest image; and applying a rolling ball filter to said second initial lung segmentation contours to smooth the shape of said second initial lung segmentation contours.

11. The medium of claim 10, wherein the computer instructions further comprise:

performing global gray-level histogram analysis of said posteroanterior chest radiographic image to identify a maximum gray-level and a minimum gray-level designating a gray-level threshold range;

and wherein the computer instructions for said performing global threshold analysis further comprise:
a) generating a binary image having pixels having either a first logic level or a second logic level based on a gray-level threshold within said gray-level threshold range;
b) repeating substep a) a predetermined number of times at progressively larger gray-level thresholds within the gray-level threshold range; and
c) processing said binary image to eliminate pixels outside the lung fields.

12. The medium of claim 10, wherein the computer instructions for said performing local threshold analysis comprise:

positioning regions-of-interest (ROIs) along said first initial lung segmentation contours;

performing local gray-level thresholding within each of said ROIs;

generating a composite binary image based on said performing local gray-level thresholding; and constructing based on said composite binary image said second initial lung segmentation contours for said posteroanterior chest image.

13. The medium of claim 10, wherein the computer instructions further comprise:

delineating costophrenic angle margins for each of said lung fields; and constructing final lung segmentation contours based on said first initial lung segmentation contours and said costophrenic angle margins.

14. The medium of claim 13, wherein the computer instructions for said constructing final lung segmentation contours comprise:

splicing said costophrenic angle margins to said second initial lung segmentation contours to construct said final lung segmentation contours.

15. The medium of claim 13, wherein the computer instructions for said delineating costophrenic angle margins comprises:

determining whether said posteroanterior chest image exhibits an abnormal hemithorax.

16. A computer readable medium storing computer instructions for identification of lung fields within a chest region based on posteroanterior chest radiographic images, by performing the steps of:

generating first image data representative of a posteroanterior chest image inclusive of lung fields;

performing global threshold analysis of the posteroanterior chest image;

constructing, based on said global threshold analysis, first initial lung segmentation contours for said posteroanterior chest image; and performing global gray-level histogram analysis of said posteroanterior chest radiographic image to identify a maximum gray-level and a minimum gray-level designating a gray-level threshold range;

wherein the computer instructions for said performing global threshold analysis further comprise:

a) generating a binary image having pixels having either a first logic level or a second logic level based on a gray-level threshold within said gray-level threshold range, b) repeating substep a) a predetermined number of times at progressively larger gray-level thresholds within the gray-level threshold range, and c) processing said binary image to eliminate pixels outside the lung fields;

wherein the computer instructions for said substep c) comprise:

constructing intermediate lung segmentation contours representing boundaries of groups of contiguous pixels having said first logic level, determining the centroid for each of said intermediate lung segmentation contours;

detecting centroids outside the lung fields based on a gray-level profile, and prohibiting regions of the binary image defined by intermediate lung segmentation contours having centroids outside the lung fields from having said first logic level during subsequent iterations of said generating a binary image.

17. The medium of claim 16, wherein the computer instructions for said performing global threshold analysis further comprise:

smoothing the intermediate lung segmentation contours constructed during the last iteration of said generating a binary image to provide said first initial lung segmentation contours.

18. A computer-readable medium storing computer instructions for identification of lung fields within a chest region based on posteroanterior chest radiographic images, by performing the steps of:

generating first image data representative of a posteroanterior chest image inclusive of lung fields;

performing global threshold analysis of the posteroanterior chest image;

constructing, based on said lung fields identified in said processed image global threshold analysis, first initial lung segmentation contours for said posteroanterior chest image;

delineating costophrenic angle margins for each of said lung fields; and constructing final lung segmentation contours based on said first initial lung segmentation contours and said costophrenic angle margins;

wherein the computer instructions for said delineating costophrenic angle margins comprise:

a) placing costophrenic regions of interest (ROIs) over approximate locations of each costophrenic angle as determined based on the first initial lung segmentation contours;

b) identifying diaphragm border points within each of said ROIs;

c) identifying costal border points within each of said ROIs;

d) checking the placement of said ROIs at least once to determine whether the ROIs were positioned accurately in substep a); and e) repeating substeps a) through d) if it is determined in substep d) that the ROIs were not accurately positioned in substep a).

19. A system for identifying lung fields within a chest region based on posteroanterior chest radiographic images, comprising:

an image acquisition device configured to generate first image data representative of a posteroanterior chest image inclusive of lung fields;

a global gray-level thresholding unit configured to perform global threshold analysis of the posteroanterior image;

means for constructing, based on said global threshold analysis, first initial lung segmentation contours for said posteroanterior chest image;

a local gray-level thresholding unit configured to perform, based on said first initial lung segmentation contours, local threshold analysis to construct second initial lung segmentation contours for said posteroanterior chest image; and a rolling ball filter unit configured to apply a rolling ball filter to said second initial lung segmentation contours to smooth the shape of said second initial lung segmentation contours.

20. The system of claim 19, further comprising:

a gray-level histogram analysis unit configured to perform a global gray-level histogram analysis of said posteroanterior chest radiographic image to identify a maximum gray-level and a minimum gray-level which designate a gray-level threshold range;

wherein said global gray-level thresholding unit comprises:

a) means for generating a binary image with pixels having either a first logic level or a second logic level based on a gray-level threshold within said gray-level threshold range;

b) means for iteratively using said a) means a predetermined number of times at progressively larger gray-level thresholds within the gray-level threshold range; and c) means for processing said binary image to eliminate pixels outside the lung fields.

21. The system of claim 19, wherein said local gray-level thresholding unit further comprises:

means for positioning regions-of-interest (ROIs) along said first initial lung segmentation contours;

means for performing local gray-level thresholding within each of said ROIs;

means for generating a composite binary image based on an output of said means for performing local gray-level thresholding; and means for constructing based on said composite binary image said second initial lung segmentation contours for said posteroanterior chest image.

22. The system of claim 19, further comprising:

means for delineating costophrenic angle margins for each of said lung fields; and means for constructing final lung segmentation contours based on said first initial lung segmentation contours and said costophrenic angle margins.

23. The system of claim 22, wherein said means for constructing final lung segmentation contours comprises:

a splicing unit configured to splice said costophrenic angle margins to said second initial lung segmentation contours to construct said final lung segmentation contours.

24. The system of claim 22, wherein said means for delineating costophrenic angle margins comprises:

means for determining whether said posteroanterior chest image exhibits an abnormal hemithorax.

25. A system for identifying lung fields within a chest region based on posteroanterior chest radiographic images, comprising:

an image acquisition device configured to generate first image data representative of a posteroanterior chest image inclusive of lung fields;

a global gray-level thresholding unit configured to perform global threshold analysis of the posteroanterior image;

means for constructing, based on said global threshold analysis, first initial lung segmentation contours for said posteroanterior chest image;

a gray-level histogram analysis unit configured to perform a global gray-level histogram analysis of said posteroanterior chest radiographic image to identify a maximum gray-level and a minimum gray-level which designate a gray-level threshold range;

wherein said global gray-level thresholding unit comprises:
  a) means for generating a binary image with pixels having either a first logic level or a second logic level based on a gray-level threshold within said gray-level threshold range,
  b) means for iteratively using said a) means a predetermined number of times at progressively larger gray-level thresholds within the gray-level threshold range, and
  c) means for processing said binary image to eliminate pixels outside the lung fields;
  wherein said c) means comprises:
    means for constructing intermediate lung segmentation contours representing boundaries of groups of contiguous pixels having said first logic level,
    means for determining the centroid for each of said intermediate lung segmentation contours,
    means for detecting centroids outside the lung fields based on a gray-level profile, and
    means for prohibiting regions of the binary image defined by intermediate lung segmentation contours with centroids outside the lung fields from having said first logic level during subsequent iterations of using said a) means.

26. The system of claim 25 wherein said global gray-level thresholding analysis unit further comprises:

means for smoothing the intermediate lung segmentation contours constructed during the last iteration of using said a) means to provide said first initial lung segmentation contours.

27. A system for identifying lung fields within a chest region based on posteroanterior chest radiographic images, comprising:

an image acquisition device configured to generate first image data representative of a posteroanterior chest image inclusive of lung fields;

a global gray-level thresholding unit configured to perform global threshold analysis of the posteroanterior image;

means for constructing, based on said global threshold analysis, first initial lung segmentation contours for said posteroanterior chest image;

means for delineating costophrenic angle margins for each of said lung fields; and means for constructing final lung segmentation contours based on said first initial lung segmentation contours and said costophrenic angle margins;

wherein said means for delineating costophrenic angle margins comprises:
  a) means for placing costophrenic regions of interest (ROIs) over approximate locations of each costophrenic angle as determined based on the first initial lung segmentation contours;
  b) means for identifying diaphragm border points within each of said ROIs;
  c) means for identifying costal border points within each of said ROIs;
  d) means for checking the placement of said ROIs at least once to determine whether the ROIs were positioned accurately by said a) means; and
  e) means for iteratively using means a) through d) if it is determined by d) means that the ROIs were not accurately positioned by said a) means.

* * * * *

UNITED STATES PATENT AND TRADEMARK OFFICE
CERTIFICATE OF CORRECTION

PATENT NO. : 6,282,307 B1
DATED : August 28, 2001
INVENTOR(S) : Samuel G. Armato, III et al.

It is certified that error appears in the above-identified patent and that said Letters Patent is hereby corrected as shown below:

Column 11,
Line 9, change "comer" to -- corner --.

Column 13,
Line 19, change "O=normal" to -- 0=normal --;
Line 20, change "I=slightly" to -- 1=slightly --;
Line 50, change "O0.83" to -- 0.83 --.

Signed and Sealed this

Twelfth Day of March, 2002

Attest:

Attesting Officer

JAMES E. ROGAN
Director of the United States Patent and Trademark Office